United States Patent
McDonald et al.

(10) Patent No.: US 8,926,651 B2
(45) Date of Patent: Jan. 6, 2015

(54) SELF-LOCKING TOURNIQUET AND AUTOMATED TIMER

(76) Inventors: Rex McDonald, London, KY (US); Hanners Gevedon, Mt. Vernon, KY (US); John Eaton, Mount Vernon, KY (US)

(*) Notice: Subject to any disclaimer, the term of this patent is extended or adjusted under 35 U.S.C. 154(b) by 392 days.

(21) Appl. No.: 13/232,397

(22) Filed: Sep. 14, 2011

(65) Prior Publication Data

US 2012/0071917 A1    Mar. 22, 2012

Related U.S. Application Data

(60) Provisional application No. 61/465,488, filed on Mar. 21, 2011, provisional application No. 61/403,308, filed on Sep. 14, 2010.

(51) Int. Cl.
| | | |
|---|---|---|
| A61B 17/132 | (2006.01) | |
| G01L 5/10 | (2006.01) | |
| G01L 5/04 | (2006.01) | |
| A61B 19/00 | (2006.01) | |
| A61B 17/00 | (2006.01) | |

(52) U.S. Cl.
CPC ....... *A61B 17/1322* (2013.01); *A61B 2019/464* (2013.01); *G01L 5/102* (2013.01); *A61B 2017/00132* (2013.01); *A61B 2017/00115* (2013.01); *G01L 5/047* (2013.01)
USPC .......................................... 606/203; 606/201

(58) Field of Classification Search
None
See application file for complete search history.

(56) References Cited

U.S. PATENT DOCUMENTS

| | | | |
|---|---|---|---|
| 4,243,039 A * | 1/1981 | Aginsky | 606/203 |
| 4,321,929 A | 3/1982 | Lemelson et al. | |
| 6,746,470 B2 | 6/2004 | McEwen et al. | |
| 6,899,720 B1 | 5/2005 | McMillan | |
| 7,842,067 B2 | 11/2010 | Esposito | |
| 2003/0139766 A1 | 7/2003 | McEwen | |
| 2005/0240217 A1 | 10/2005 | Jennifer et al. | |
| 2006/0089668 A1 * | 4/2006 | Warburton | 606/203 |
| 2008/0146980 A1 | 6/2008 | Rousso et al. | |
| 2008/0177159 A1 | 7/2008 | Gavriely | |
| 2008/0312682 A1 | 12/2008 | Shams | |
| 2009/0062842 A1 * | 3/2009 | Esposito et al. | 606/203 |
| 2009/0062843 A1 | 3/2009 | Heston | |
| 2010/0057120 A1 | 3/2010 | Kirkham | |
| 2010/0160957 A1 | 6/2010 | Kirkham | |
| 2010/0234877 A1 | 9/2010 | Pienkowski et al. | |

OTHER PUBLICATIONS

U.S. Appl. No. 61/465,488, filed Mar. 21, 2011.

(Continued)

*Primary Examiner* — Melanie Tyson
*Assistant Examiner* — Todd J Scherbel
(74) *Attorney, Agent, or Firm* — Stockwell & Smedley, PSC

(57) ABSTRACT

Tourniquet assemblies are provided including a pressure applicator adapted to be secured around a limb and a tensioning mechanism for applying a working tension to the pressure applicator. The tensioning mechanism may include a platform, a clip and a tensioning member. The tensioning mechanism may be configured to apply the working tension via rotation of the tensioning member, and the clip may be configured to receive, and at least temporarily inhibit rotation of, the tensioning member. A tension indicator may also be provided including a base configured to attach to a tourniquet strap, a platform configured to move relative to the base when subjected to a tourniquet working pressure, and one or more tactile or visual indicators configured to provide a variable tactile or visual indicator based on the tourniquet working pressure.

8 Claims, 23 Drawing Sheets

(56) References Cited

OTHER PUBLICATIONS

U.S. Appl. No. 61/403,308, filed Sep. 14, 2010.

International Search Report corresponding to the PCT/US2012/055418 application.

International Preliminary Report on Patentability mailed Mar. 27, 2014 for PCT/US12/055418.

* cited by examiner

SELF-LOCKING TOURNIQUET AND AUTOMATED TIMER

CROSS-REFERENCES TO RELATED APPLICATIONS

This application claims benefit under 35 U.S.C. §119(e) to provisional application Ser. Nos. 61/465,488, filed on Mar. 21, 2011, and 61/403,308, filed on Sep. 14, 2010, the disclosures of which are hereby incorporated herein by reference in their entireties.

BACKGROUND OF THE INVENTION

1. Field of the Invention

The invention relates generally to tourniquets. More particularly, aspects of the invention include tourniquets with self-locking features, and/or tourniquet timers that provide visual and tactile indicators based on pressure applied to the tourniquet.

2. Related Art

As known in the art, and as variously described in various of the below-identified references, a tourniquet is a device that is designed to be applied to a limb for the purpose of constricting blood flow to that limb by applying pressure in order to limit the effects of extreme blood loss.

Tourniquets are typically used in the temporary treatment of extremity injuries, i.e. damage to the body's arms and legs. The severity of an extremity injury depends on the location and path of the injury. Critical conditions are commonly associated with compromised vascular components of the particular extremity. Vascular injuries to the extremities become critical when life threatening blood loss is possible.

When a major artery is severed, either by injury or surgical intervention, controlling blood loss becomes vital. In severe cases, where potential blood loss is considered life-threatening, a tourniquet may be applied proximal to the vascular disruption to manage blood loss. Because of its rapid blood flow occlusion capabilities, the tourniquet is commonly considered a life-saving device in emergency situations.

Even though civilian extremity injuries are common, extremity injuries occurring in the battlefield are more frequent and can present unique challenges. Therefore, many emergency tourniquets are specialized for use on the battlefield. In general, the goal of such tourniquets is to extend the survival time of a casualty until the patient can reach additional medical aid.

Knowledge of tourniquet application time serves as a determining factor for the method of treatment once an individual reaches a medical facility. Specifically it allows clinicians to estimate the amount of blood loss and the extent of the extremity injury. Based upon tourniquet application time and other signs, e.g. hematoma, hemorrhage, or acute ischemia, the patient will be diagnosed and the severity of injury will be scored using the injured extremity index. Monitoring application time is also important with regard to the side effects of tourniquet application and may also play a part in determining the extent of an extremity injury.

Tourniquet application time is also important to account for readjustment periods. A tourniquet must remain extremely taught to prevent severe blood loss. However, extreme pain is commonly associated with blood occlusion caused by a tourniquet. The pain, caused by hypoxia becomes so extensive in certain cases that some victims loosen the tourniquet to allow some blood flow distal to the tourniquet application site which therefore alleviates some of the pain. The individual later retightens the tourniquet. This process may occur multiple times over the period of transportation to a medical facility. However, when the individual reaches medical help this information is rarely transferred to the medics even though the non-uniform occlusion may alter the treatment plan.

The pressure applied by an emergency tourniquet may in some configurations be controlled by the user. Pain associated with tourniquet application or accompanying injuries, may prevent or inhibit an individual from tightening the tourniquet to the proper level. Also, the user may not know the appropriate tension to occlude severe blood loss.

U.S. Pat. No. 4,321,929 to Lemelson, et al. describes an automatic tourniquet with a control system. An electronic sensing means senses physiological variables and generates signals which are applied to the computer or microprocessor, which analyzes such signals and generates control signals for controlling the motors operating pumps. A timer is provided for controlling the automatic tourniquet and providing intervals of time during which blood pressure is sensed and the tourniquet is tightened.

U.S. Pat. No. 6,746,470 describes a pneumatic tourniquet adapted for self application. In particular, the tourniquet comprises a bladder cuff with a clamp means for securing the bladder around the limb and an indicator module connected to the bladder. The indicator module indicates cuff pressure and elapsed inflation time interval and is supplied with a microprocessor and an alarm indicator that provides an audible and visual indication of alarm. The microprocessor is programmed to determine elapsed inflation time by measuring the duration of time that the pressure has exceeded a predetermined pressure threshold. The alarm indicator may also be activated by microprocessor if unusually high pressures are detected in the bladder (for example pressures greater than 400 mmHg).

U.S. Patent Application Publication No. 2010/0234877 by Pienkowski et al. describes an "electromechanical" tourniquet with a force sensor to measure occlusive pressure applied along a line extending into the limb of a person as well as a user interface that displays duration of use. The tourniquet includes a microcontroller connected to the force sensor as well as a battery and a voltage regulator. A power button of the tourniquet may be activated and an extremity selector switch set to define the extremity and/or location of tourniquet application.

U.S. Patent Application Publication No. 2008/0177159 by Gavriely describes a timer for tourniquets that generates two or more warnings, for example, both an advance warning that a usage time is about to expire and a final warning when a usage time expires and a danger time begins. The generating of the first and/or the second warning may be accompanied by sound and/or light signals, and/or a wireless transmitted warning.

U.S. Patent Application Publication No. 2010/0160957 by Kirkham describes a one-handed loop tourniquet that includes an elongate cord and a cleat with at least two recesses for receiving and securing an end of the elongate cord during use as a tourniquet. In use, the free end of the cord is passed through a loop of the cord so that the cord extends around the limb to which the tourniquet is being applied, and then the free end of the cord is locked into the cleat using the recesses.

Despite many advances in the design and use of tourniquets, there still exist limitations in the effectiveness of various implementations, particularly in the context of rapid and reliable application and monitoring of the tourniquet in conditions that may typically be found on the battlefield and other emergency situations. For example, the use of various known electronic monitoring and control means may be susceptible to shock, pressure, moisture, dirt, etc. routinely found in battlefield conditions. Other tourniquet configurations that may be adapted for one person to use may also suffer from drawbacks in their performance, and/or clinical effectiveness, due to accommodations made to suit one-handed use. For example, the cord tourniquet such as described in Kirkham, and other known means, may lack the desired ability to properly set and/or distribute the necessary pressure applied by the tourniquet to effectively stop extremity bleeding including arterial bleeding.

Accordingly, there exist ongoing needs for improved tourniquet devices that are adapted for on-hand use and/or include robust, and easy to use, reuse and/or monitor, timing devices.

BRIEF SUMMARY OF THE INVENTION

The invention provides various embodiments of tourniquets, tensioning and self-locking mechanisms, and timing devices. The invention may be implemented in a number of ways.

In embodiments, exemplary tourniquets may be configured to allow application to a patient with a single hand. A tensioning mechanism may allow the tourniquet to be tightened and the tensioning system locked into position. Embodiments may include various means that set a timing system that can be visually and/or physically inspected to assist in determining when the tourniquet has been applied and/or for how long tension has been applied to the tourniquet.

According to aspects of the invention, tourniquets and associated timing devices may be provided that are relatively small, compact, user-friendly and robust. Due to various design aspects, tourniquets as described herein may be capable of applying a variety of different diameters and varying amounts of pressure upon the limb for the purpose of decreasing or stopping blood flow to the affected limb.

Various tourniquet timing features described herein may be designed so that, once activated, a small indicator pin or the like is released thereby showing tension has been applied. For example, when an oversized pin has been pulled through a restrained opening, it may expose the pin for visual and tactile recognition. Moreover, when the pin or the like is peeled away from a backing strip, it may be expose to oxygen, initiating a chemical action that may begin acting as a timer that shows the length of time since the pin has been displaced. In embodiments, the timer may be configured to change color over time indicating the length of time the tourniquet has been applied.

In embodiments, tension indicators and the like may be further configured to allow tension to be applied to multiple sides of a device via a strap or other external mechanism as well as to indicate the amount of time and the degree of pressure being used. Tension applied to the device may cause, for example, an internal mechanism to physically move allowing the activation of a timing device. Devices such as those described herein may be utilized in any situation where tension needs to be applied to a strap or other physical member and then be maintained regardless of minor changes in the straps circumference.

According to further aspects of the invention, a tourniquet assembly may be provided including one or more of a pressure applicator adapted to be secured around a limb; a tensioning mechanism for applying a working tension to the pressure applicator, a clip and a tensioning member; and/or a tension indicator. In embodiments, the tensioning mechanism may be configured to apply the working tension via rotation of the tensioning member. In embodiments, the clip may be configured to receive, and at least temporarily inhibit rotation of, the tensioning member.

In embodiments, the pressure applicator may include a plurality of strips, such as a tensioning strip, a main webbing strip and/or a hook and loop strip. In embodiments, a tensioning strip may be received through the tensioning member.

In embodiments, the tensioning mechanism may include a platform. In embodiments, the platform may include at least one first slot sized to receive at least part of the pressure applicator therethrough.

In embodiments, the first slot may be disposed toward one end of the platform and the clip may be disposed toward the other end of the platform. The tensioning member, or a rotational axis of the tensioning member, may be disposed between the first slot and the clip.

In embodiments, the clip may be configured to transition from an open configuration that allows the tensioning member to be received in the clip, to a closed configuration that holds the tensioning member from being released from the clip.

In embodiments, the clip may include opposing flexible walls and a pair of opposing flanges disposed on free ends of respective opposing walls, each of said flanges being configured to selectively engage with the other opposing flange to at least temporarily secure the clip in the closed configuration.

In embodiments, the clip may include a slot for receiving the tensioning member and a flap configured to close the slot in the closed configuration.

In embodiments, the tension indicator may include one or more of a base configured to attach to the pressure applicator, a platform configured to move relative to the base when subjected to the working tension, a tactile indicator configured to provide a variable tactile indicator based on relative lateral motion of the platform to the base, a visual indicator configured to provide a variable visible indicator based on the working tension, and/or an initiator configured to apply a variable pressure to the visual indicator based on relative lateral motion of the platform to the base.

In embodiments, the visual indicator may include one or more of a reservoir, a timing strip, and/or a seal between the reservoir and the timing strip. The initiator may include a moveable member, such as a roller, a sphere, a wedge or asymmetrical rotating member, that is configured to apply variable pressure to the reservoir via vertical displacement of the moveable member in response to the relative lateral motion of the platform to the base.

In embodiments, the pressure applied to the reservoir via the moveable member may be operable to force a fluid contained in the reservoir through the seal and into communication with the strip.

The device has a physical and visual indicator that shows the pressure applied. Other internal features allow a tension, once applied, to be maintained over a short-range of movement while being gauged by a visual and tactile indicator.

According to yet further aspects of the invention, a tourniquet tension indicator may be provided including one or more of a base configured to attach to a tourniquet strap, a platform configured to move relative to the base when subjected to a tourniquet working pressure, a tactile indicator configured to provide a variable tactile indicator based on relative lateral motion of the platform to the base, a visual indicator configured to provide a variable visible indicator based on the tourniquet working pressure, and/or an initiator configured to apply a pressure to the visual indicator based on relative lateral motion of the platform to the base.

Embodiments may include a compressible member disposed substantially in-plane with the platform. The compressible member may be configured, for example, to resist movement of the platform relative to the base when tension is applied to the tourniquet and/or to provide the working pressure before becoming fully compressed.

Embodiments may include a top cover, and the platform may be slideably mounted between the top cover and the base. In embodiments, at least one of the top cover, the platform and the base may include a slot through which the tactile indicator may be viewed and felt, and the tactile indicator may be configured to move laterally in the slot as the compressible member is compressed.

In embodiments, the initiator may include, for example, a moveable roller that is configured to displace vertically in response to lateral relative motion between the platform and the base, and to apply pressure to the reservoir via vertical displacement of the roller. In this regard, it should be understood that vertical displacement is not intended to exclude the roller from moving in a lateral direction. In fact, according to various embodiments described herein, relative and/or actual lateral movement of the moveable and/or rolling members may be used to encourage the vertical displacement thereof.

In embodiments, at least one of the platform and the base may include a track accommodating the moveable member and/or roller, the track including at least one of a ramp or a step that forces the roller to move vertically in response to the lateral relative motion between the platform and the base. As used herein "steps" should be understood as encompassing various shapes, including, for example, rounded, converse, convex angled and other configurations in which there is a marked change in the height profile that can be used to urge the moveable member and/or roller in the vertical direction.

In embodiments, the pressure applied to the reservoir via the rotating member may be operable to force a fluid contained in the reservoir through the seal and into communication with the strip.

In embodiments, the reservoir and the timing strip may be included in a discreet removable package, which may include an adhesive strip configured to at least temporarily attach the package to at least one of a top cover, a base and a platform included in the tension indicator.

Embodiments may include a top cover, wherein the platform is slideably mounted between the top cover and the base. The tactile indicator may include a post that is visible, and can be felt, though a slot in the top cover. In embodiments, the visual indicator may be secured to the top cover.

In embodiments, the tactile indicator may include a plurality of graduations indicative of different tensions applied to the tourniquet tension indicator.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
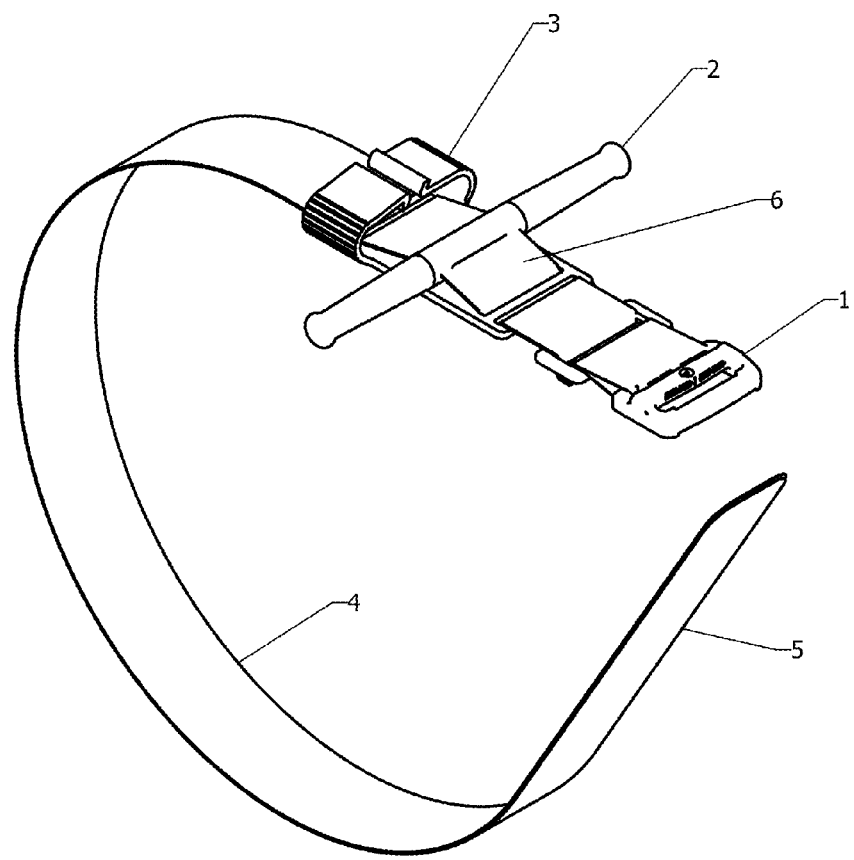
FIG. 1 is an isometric view of a first embodiment of a tourniquet assembly according to aspects of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a strap" is a reference to one or more straps and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

The term "vertically" as used herein generally refer to upward and downward directions when observing components, e.g. buckles, etc. from a side view.

The terms "laterally" or "horizontally" as used herein generally refer to directions substantially perpendicular to the vertical direction when observing components, e.g. buckles, etc. from a side view.

The terms "active agent," "drug," "therapeutic agent," and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect. In particular, the therapeutic agent may encompass a single biological or abiological chemical compound, or a combination of biological and abiological compounds that may be required to cause a desirable therapeutic effect.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The terms "condition," "disease" and "disorder" are used interchangeably herein as referring to a physiological state that can be detected, prevented or treated by the surgical techniques, devices and/or therapeutic agent as described herein.

The term "patient" as in treatment of "a patient" refers to a mammalian individual afflicted with or prone to a condition, disease or disorder as specified herein, and includes both humans and animals.

The term "working tension" includes tension sufficient for temporary treatment of extremity injuries as known to those of skill in the art and can vary based on, for example, the width of the tourniquet and the circumference of the affected limb. Working tensions may vary, unless otherwise specified, in ranges that provide partial to near-complete occlusion.

FIG. 1 shows a first embodiment of an exemplary tourniquet assembly according to aspects of the invention. As shown in FIG. 1, a buckle 1 allows the tourniquet to form a loop by inserting a free end through buckle 1 and folding back upon itself. FIG. 1 also shows a tensioning mechanism including rod 2 with tensioning webbing 6 that is inserted through a slot in rod 2. Tensioning webbing 6 may be configured to travel inside a slot throughout the entire sewn structure of the tourniquet so when rod 2 is twisted, the force will apply a tension along its length thereby constricting the tourniquet strap.

Embodiments may also include a clip, such as Clip 3 shown in FIG. 1, that is configured to receive and/or temporarily restrain a tensioning member, such as bar 2. For example, clip 3 may be configured such that, when rod 2 has been twisted to generate the desired working tension on tensioning webbing 6, the end of the rod 2 can be received by clip 3.

Embodiments may also include a main webbing strip, such as the back webbing strip 4 shown in FIG. 1, which is typically a piece of high strength woven strapping material. FIG. 1 shows front hook and loop strip 5, which may include material that contains cooperating hooks and loops woven into its surface. When the front hook and loop strip 5 are placed through buckle 1, the free end may be attached back to the loop strip 5 forming a secure loop through the buckle 1. A twisting action applied to rod 2 will then allow tensioning webbing 6 to be tightened, applying a constricting pressure to the injured limb. When sufficient pressure has been applied by twisting rod 2, the end of rod 2 can be secured into clip 3.

As shown in FIG. 1, clip 3 includes a pair of cooperating flanges on opposite sidewalls, configured to engage with one another and secure the clip in a closed configuration. In particular, clip 3 is configured to be coupled by applying pressure to the ridged flexible sidewalls, thereby allowing the angularity and locking feature of the flanges may be used to capture and hold rod 2 firmly in position, preventing the rod 2 from counter rotation.

It should be noted that the width of the pressure applicator, in particular the main webbing strip, is designed to minimize tissue damage while still allowing a constrictive force. Designs according to aspects of the invention can readily accommodate webbing of sufficient width to satisfy this criteria.

Figure 2:
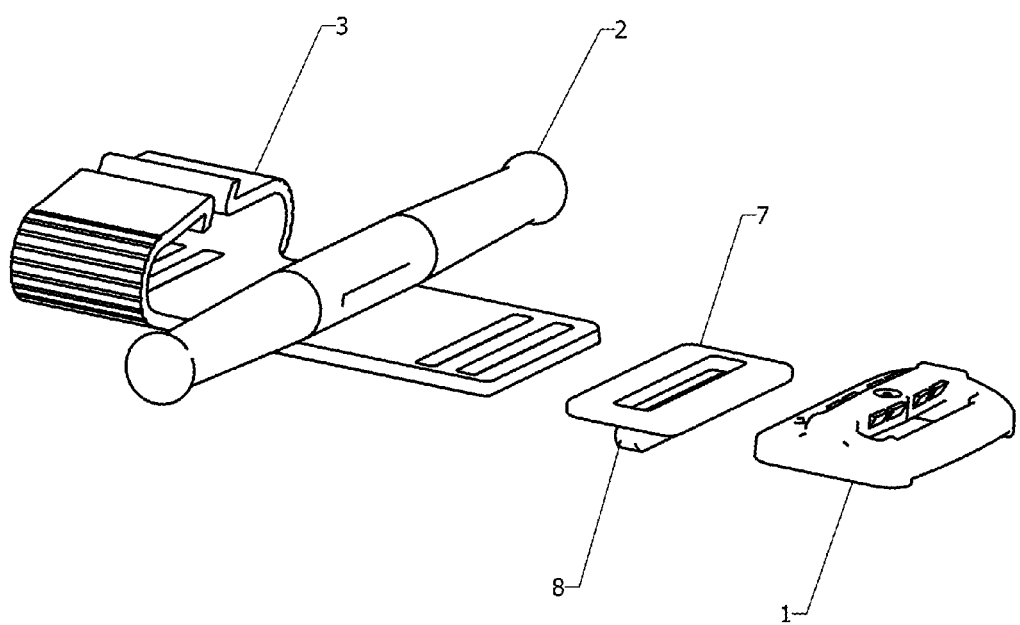
FIG. 2 is an enlarged view of an exemplary tensioning mechanism, tension indicator and buckle for use in the tourniquet assembly as shown in FIG. 1.

FIG. 2 shows additional details of the clip 3, handle 2 and buckle 1, without the strapping shown. As can be seen in FIG. 2, the locking features of clip 3 may be squeezed together and latched after rod 2 is rotated 90 degrees and received in the open slot of clip 3, thereby restraining rod 2. Buckle 1 is also shown including openings on both sides. Each of these features allow for correct positioning on the strapping. FIG. 2 further includes a tension indicator including a buckle/trap 7 and pin 8 which may be disposed between the buckle 1 and the clip 3 and associated platform. Various tension indicators that may be included according to aspects of the invention are described further below.

Figure 3:
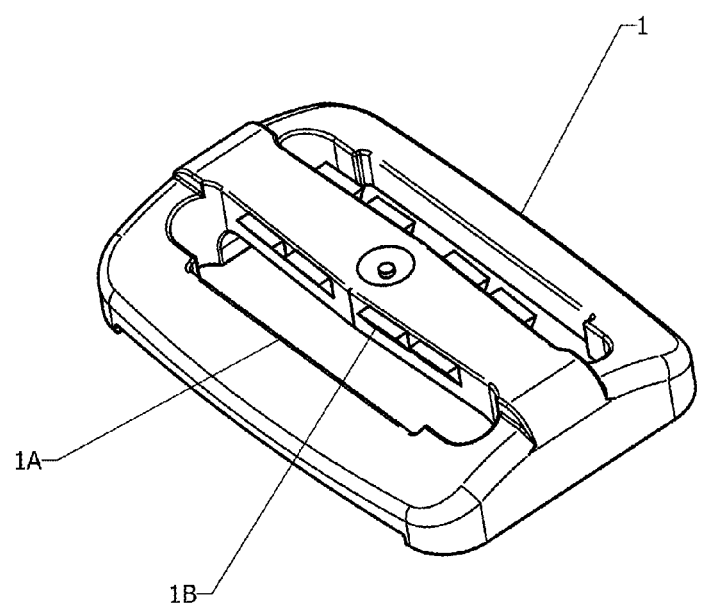
FIG. 3 is an isometric view of an exemplary buckle for use in a tourniquet assembly according to aspects of the invention.

FIG. 3 is an enlarged view of buckle 1, showing the openings located on each of its sides. These openings contain on one side items 1A, a sharp lip, and on the opposite side cleat 1B, which are features of the buckle 1. These features allow the strap to pass through the buckle to hold it into position under a tension.

Figure 4:
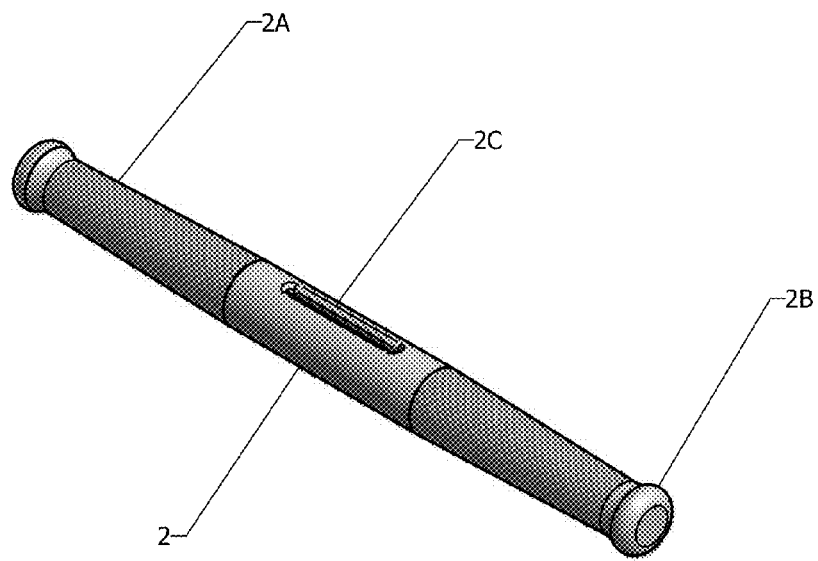
FIG. 4 is an isometric view of an exemplary tensioning member for use in a tourniquet assembly according to aspects of the invention.

FIG. 4 shows an enlarged view of rod 2, which is knurled on each end. Rod 2 also includes a slot 2C capable of allowing a piece of strapping to be passed through it or around it, allowing tension to be applied to the webbing via rotation of the rod 2. Rod 2 also has on each of its ends ball end 2B. The flared end of ball end 2B minimizes its ability to move linearly once clipped in place.

Figure 5:
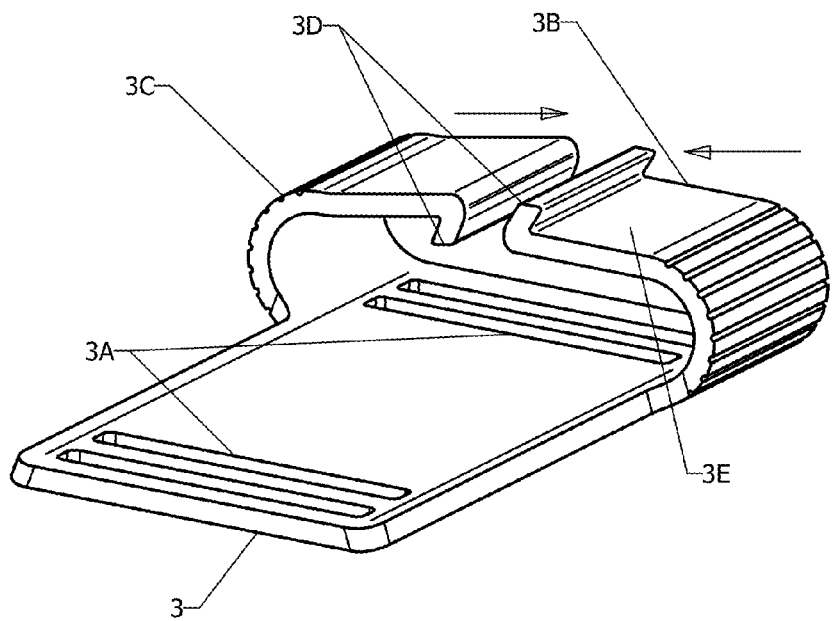
FIG. 5 is an isometric view of an exemplary clip and platform for use in a tensioning mechanism according to aspects of the invention.

FIG. 5 shows an enlarged view of clip 3. Clip 3 contains parallel slots 3A allowing strapping to be threaded through both ends of the clip. Clip 3 also includes the flex area 3B, that may be formed of a relatively thin and/or flexible material, allowing opening and closing of clip 3. Finger ridges 3C on each side of the clip 3 are ridged areas that facilitate application of compression such as by squeezing with the fingers. Locking flanges 3D shows that when these two surfaces are compressed they would interlock. Flanges 3D may be locked into position to form a trap for the rod 2 or other tensioning member, when inserted into the interior of clip 3.

FIG. 5 also shows a release area 3E that may be advantageously used to quickly release the clip 3. By a depressing release area 3E, flanges 3D may be brought out of vertical alignment, allowing the clip 3 to spring back to its original open position allowing rod 2 to be released.

Figure 6:
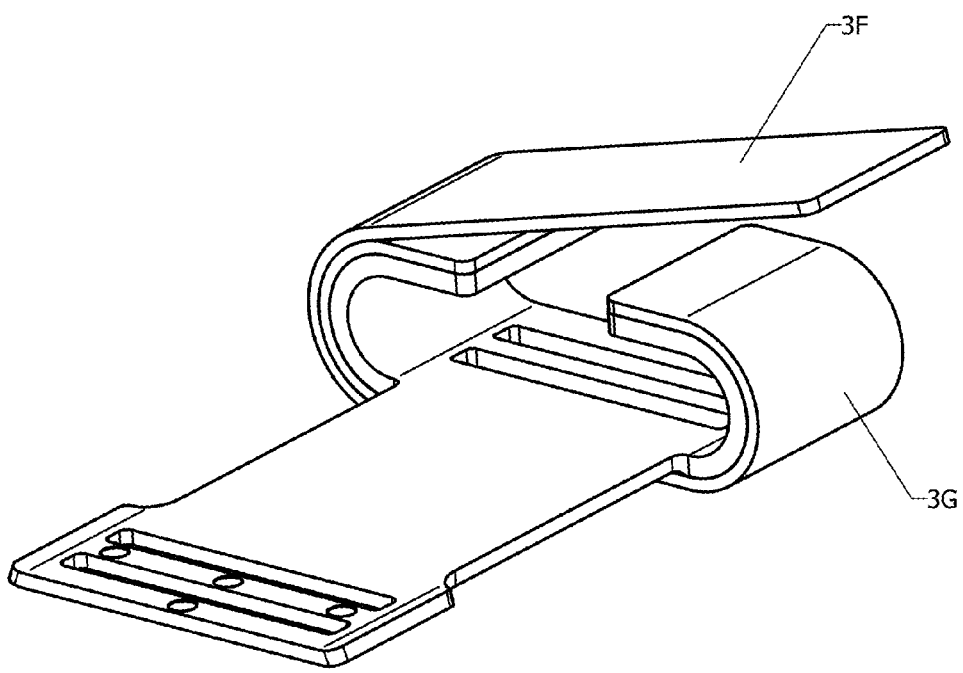
FIG. 6 is an isometric view of another exemplary clip and platform for use in a tensioning mechanism according to further aspects of the invention.

FIG. 6 shows another variation of an exemplary clip, similar to clip 3. This embodiment generally includes a flap 3F that is configured to cover the opening in the clip. The flap 3f may be configured in various ways, including manufacturing the flap from a resilient material and/or webbing with hook and loop fasteners that can fasten the flap in a closed position.

Figure 7:
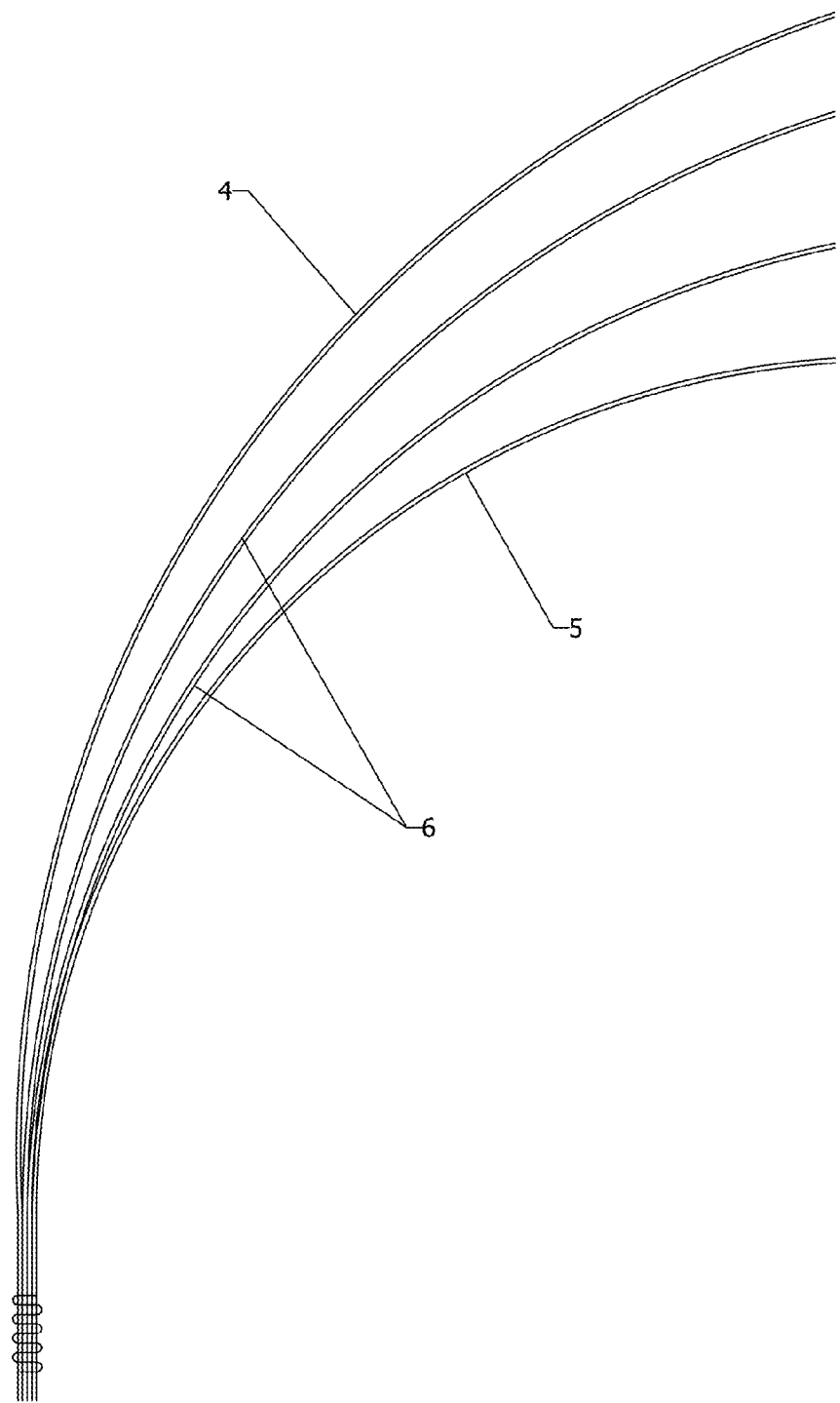
FIG. 7 depicts an exemplary pressure applicator including multiple straps for use in a tourniquet assembly according to aspects of the invention.

FIG. 7 shows details of an exemplary webbing assembly. As shown in FIG. 7, a webbing strip 4 may be configured to lie on one side of the webbing assembly, front hook and loop strip 5 may lie on an opposite side, and a loop or series of paired strips of tensioning webbing 6 may be placed in between these two layers. This may facilitate, for example, the movement of tensioning webbing 6 to apply compression forces.

Figure 8:
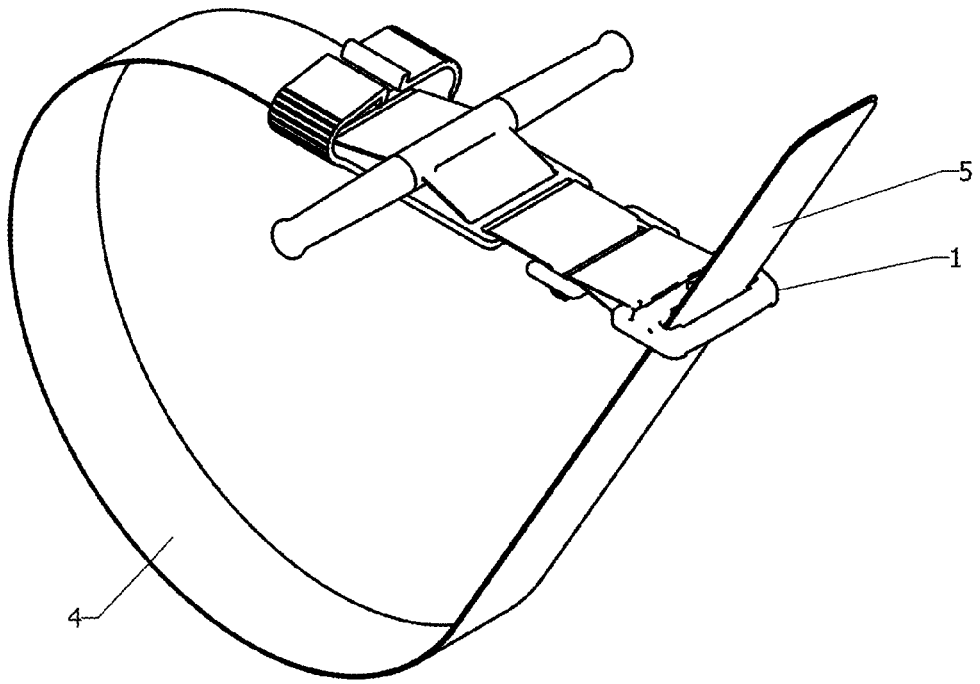
FIG. 8 is an isometric view showing an aspect of using the tourniquet assembly shown in FIG. 1 with the tension applicator fed through the buckle.

FIG. 8 shows a feature that allows the rough adjustment of diameter of the tourniquet assembly shown in FIG. 1. As shown in FIG. 8, the hook and loop Strip 5 may be assembled with the back webbing strip 4 and this assembly threaded through Buckle 1. This allows a person to decrease or increase the overall diameter of the tourniquet by moving the buckle 1 up or down this assembled strap.

Shown in FIG. 7 and again in FIG. 8 is the terminal end of hook and loop strip 5. In FIG. 7 it is referenced that these multiple layers that form hook and loop strip 5 and its assembly to back-webbing strip 4 may provide a permanent attachment of these parts together. The end of back-webbing strip 4, when it has been assembled with hook and loop strip 5 through a variety of different methods, serves a distinct function in the way that the assembly functions. The end of the assembly shown in FIG. 8 that has entered through buckle 1 has as its desired characteristic a stiffness for a short portion of the end. It also has a specific shape that will allow the end of the assembled strap portion to enter through buckle 1 easily and conveniently. It is understood that the end of this strapping could have applied to it a wide variety of different textures to facilitate in locating it in a dimly lit situation. It could also have a wide variety of colorants applied to it so that finding the slot if necessary in an emergency situation, such as in poor light to make identification easier. It is understood that adhering these ends together and shaping the ends of the strap by sewing them together and then attaching them to the strap, ultrasonically welding them into the assembly and then trimming them to a desired contour would be acceptable methods but not limited to the availability to have an auxiliary tip that could be either injection molded to join the ends of the straps or placed over it and assembled permanently in a wide variety of ways. This would allow locating that slot with the end of the strap, pushing it through, and then ultimately applying pressure while positioning the end of the strap to be made as easy as possible.

Figure 9:
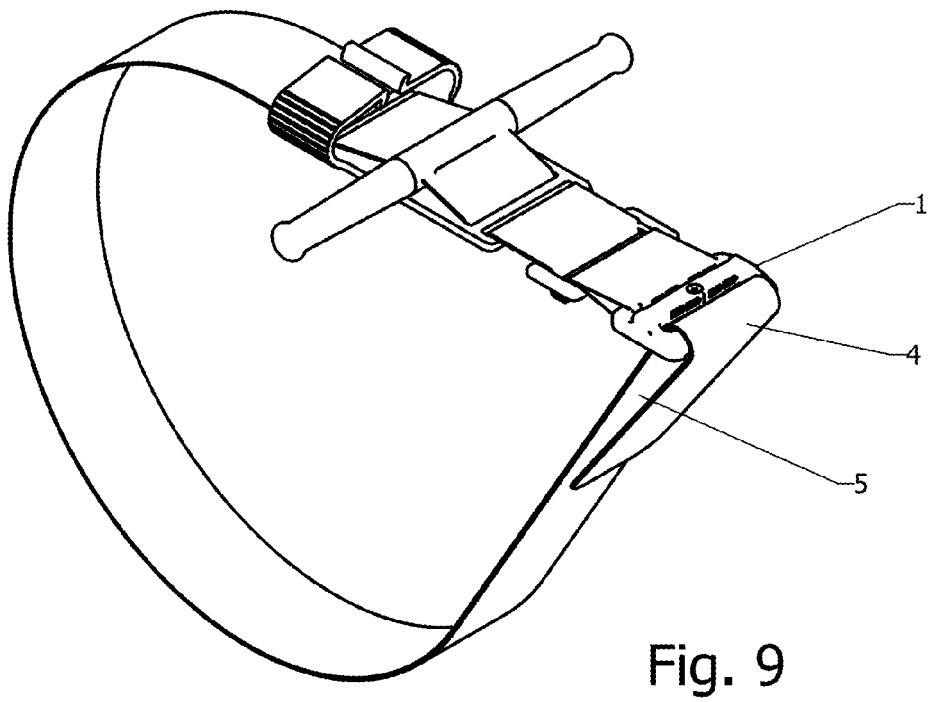
FIG. 9 is an isometric view showing further aspects of using the tourniquet assembly shown in FIG. 1 with the tension applicator secured back on itself after being fed through the buckle.

FIG. 9 shows how the strap made of assembled parts back webbing strip 4 and front hook and loop strip 5 may be folded over and affixed to itself. Once this item is folded over the sharp lip 1B on buckle 1, an anchoring point of the strap would hold itself in a secure position.

Figure 10:
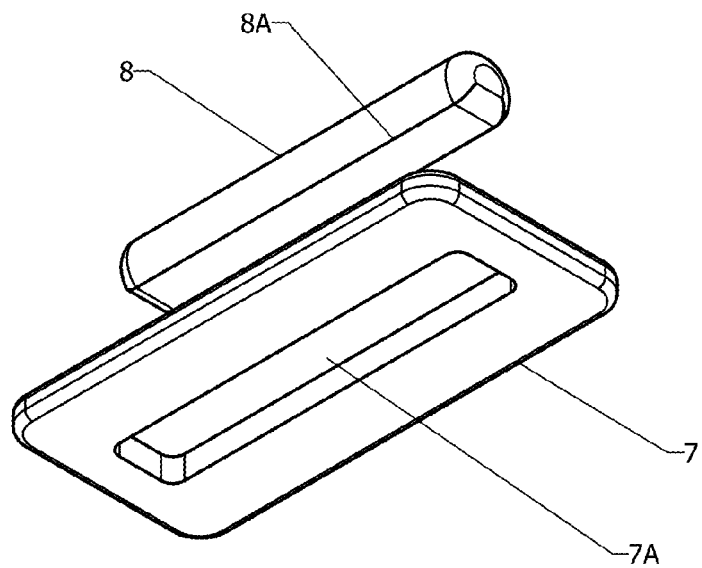
FIG. 10 is an isometric view of an exemplary tension indicator for use in a tourniquet assembly according to aspects of the invention.

FIG. 10 shows the buckle/trap 7 and its corresponding trap opening 7A. Trap 7 is designed such that, when a piece of webbing or other type of tensilary material is passed through it, the webbing may be wrapped around pin 8 and routed back through opening 7A. The opening 7A is sized and designed to allow pin 8 to be wrapped by the webbing, creating increased friction.

Figure 11:
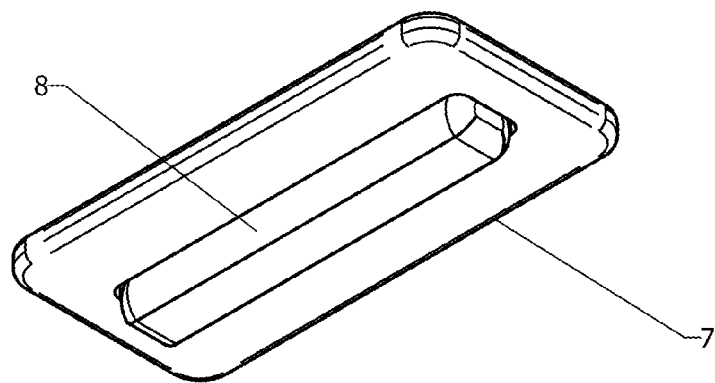
FIG. 11 depicts further details of the exemplary tension indicator shown in FIG. 10.

FIG. 11 shows pin 8 moving downward through trap 7 with the material omitted. Material or fabric may be placed in a loop around trapping pin 8 on one side of trap 7 and entering back through to the opposite side so both ends of the strap lie in the same plane of trap 7. A sufficient pressure applied to the strap in a tensile fashion pulls the pin 8 through the undersized opening 7A, and moves the pin 8 in a snapping fashion from one side of trap 7 to the opposite side of trap 7. The pin 8 may therefore provide a physical and a visual indication of tension applied to the tourniquet.

FIG. 10 also shows pin flat 8A. The bottom of pin flat 8A can be used for a wide variety of different functions. It should be understood that if any one of a wide variety of different types of visual, tactile, or auditory indicators could be coupled with the area on pin flat 8A. For example, when a predetermined tensile maximum is reached, the release of pin flat 8A through Trap 7 may allow the exposing of pin 8 so that an individual can remove pin 8 from the strip of webbing or fabric, or other sealed container, which may be useful for various purposes.

For exemplary purposes it will be described that pin flat 8A contains on its side an adhesive that contains as part of its makeup the ability to react with a chemical strip that has a visual indicator that acts as a timing mechanism. This could be achieved in a wide variety of ways but for exemplary purposes it will be explained as a visual indicator that would allow that oxygen striking a chemical agent would form a visual indicator to time of exposure to oxygen.

Figure 12:
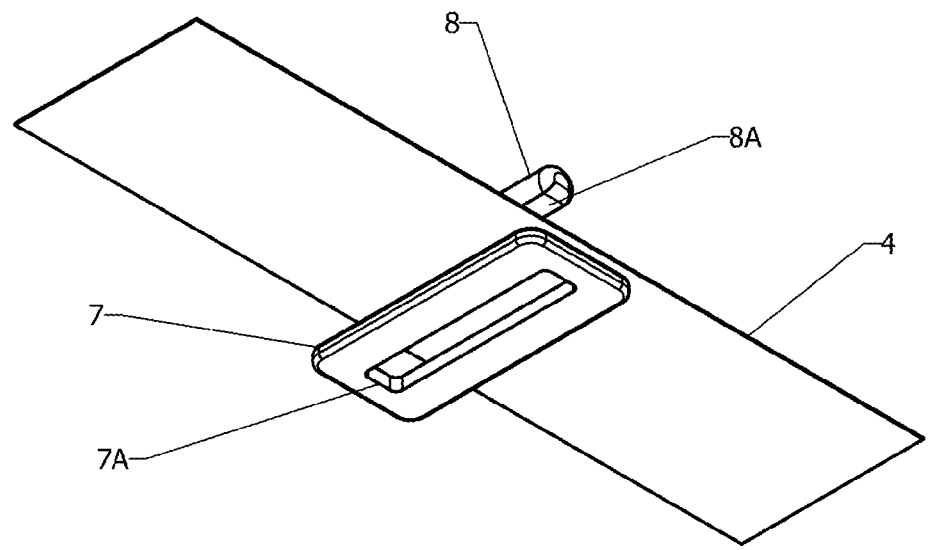
FIG. 12 depicts further details of the exemplary tension indicator shown in FIG. 10 with a strip of webbing.

FIG. 12 shows a piece of material, back webbing strip 4 upon which pin 8 and pin flat 8A have been attached for the purpose of allowing them to remain in contact while they have been assembled through trap 7 via opening 7A. This assembly allows that the chemical timer placed on the surface of pin flat 8A cannot be accessed until pin 8 has been moved through opening 7A by pressure applied to back webbing strip 4 sufficient enough to move it through the slightly undersized opening in trap 7. The force necessary to move the pin though the opening may be set to various levels depending on the desired use of the pin 8. For example, if the pin 8 includes a timer that is intended to indicate an amount of time that the tourniquet has been applied, the release force may be set to the desired working tension.

Figure 13:
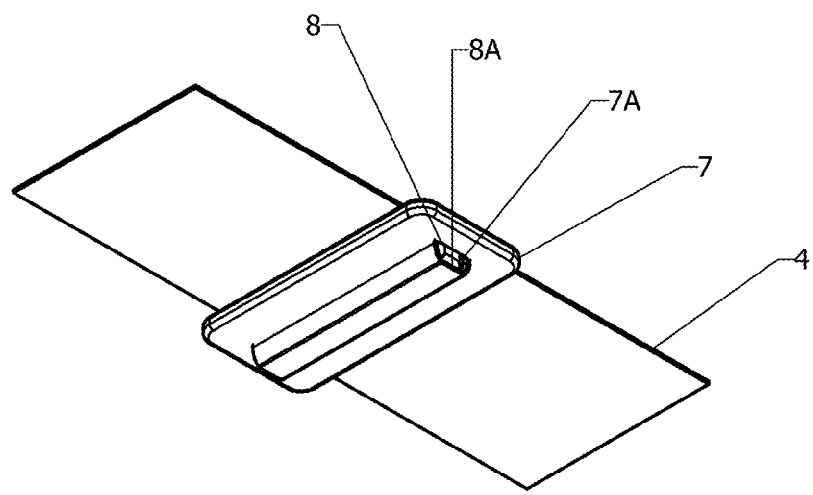
FIG. 13 depicts further details of the exemplary tension indicator shown in FIG. 10 with the strip of webbing wound through the pin and trap assembly.

FIG. 13 shows this entire assembly complete and ready for tensioning to back webbing strip 4 moving the pin 8 through the trap 7 thereby exposing it. The smaller the opening 7A in relationship to the pin 8, the more tensile pressure required to move pin 8. It can also be understood that this feature could set off a wide variety of different indicators due to the physical movement from one side to the other and is not limited merely to a chemical reaction but could be included in an electrical or other type of indication in which the removal of two parts could cause a reaction. The design of this indicator includes at least two important features, e.g. it allows a correct tension to be understood and acted on, and allows an event start point for the tourniquet.

Figure 14A:
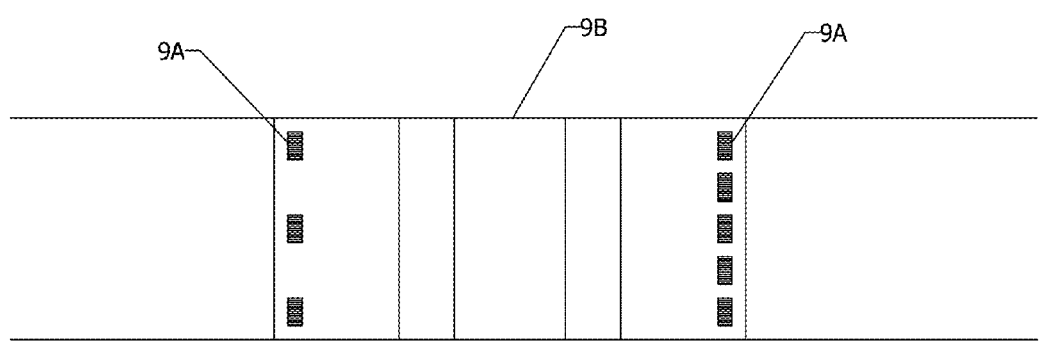
FIGS. 14A and 14B are top and side views of an exemplary pressure applicator including a strap that is folded over itself.
Figure 14B:
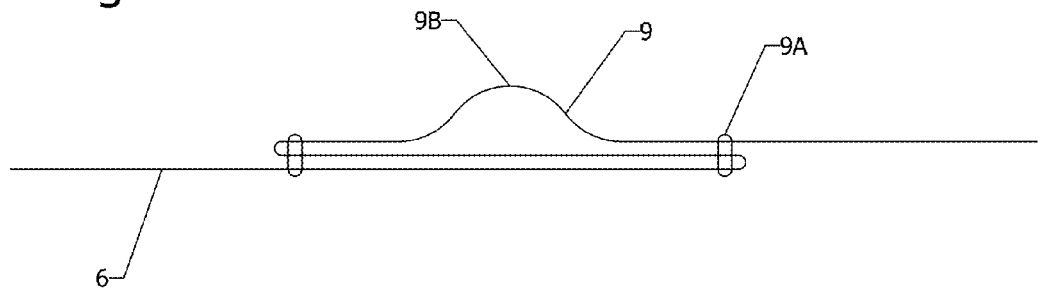

FIGS. 14A and 14B show views of another method of capturing a release or physical movement feature. It is shown that tensioning webbing 6 is tacked after having been folded in a series of layers. Tacks 9A are shown up each side of relief loop 9B. The relief loop 9B allow that tension applied to tensioning webbing 6 from each side would first overcome the tacks 9A on the right hand side. When the straps on tacks 9A are broken there would be relief in positioning of these components. The second applied tension would then make the tacks 9A on the left hand side release thereby providing a very simple and designable way to build in two pressure relief features that also contain a physical and visual indication that a given tension has been met.

Shown in FIG. 14A, the tacks 9A shown as a heavy series of hard lines along one side would maintain a much higher stretch and tensile strength than the ones shown on the opposite side therefore it follows that the number of stitches placed in the tack 9A and the proximity of the tacks to each other would make it very easy to design a system that would yield at a given tensile limit.

Tourniquets according to aspects of the invention may be designed to be easily placed around an injured limb. The strapping can be very easily adjusted to a close approximation of tension around the injured limb and that using only one hand the user can apply sufficient tension by twisting the rod 2 to allow blood flow to be stopped in case of an injury to limb. The rod 2 then can be clipped into clip 3 that allows it to remain in one position until pressure needs to be released.

Figure 15:
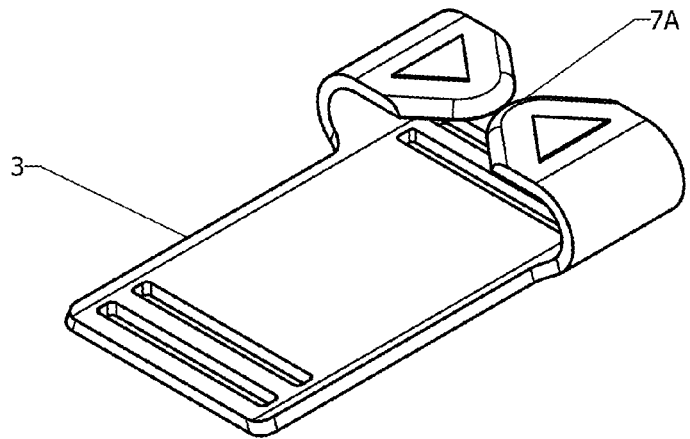
FIG. 15 is an isometric view of another exemplary clip and platform for use in a tensioning mechanism according to further aspects of the invention.

FIG. 15 shows an additional possible embodiment of a clip similar to clip 3. In the configuration shown in FIG. 15, the opening 7A is capable of merely flexing open to allow rod 2 or the like to enter therethrough. In this embodiment, the curved sidewalls may be considered sufficient to restrain the tensioning member within the clip during normal operation, without having to securely close the clip.

Figure 16:
FIG. 16 is an isometric view of the clip and platform shown in FIG. 15 with an exemplary tensioning member according to further aspects of the invention.
Figure 16:
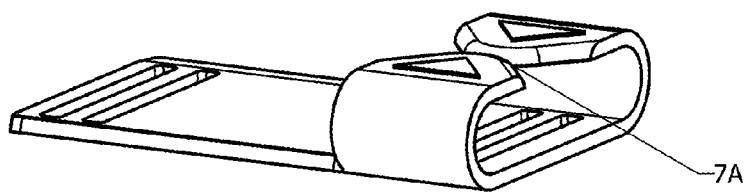

FIG. 16 shows rod 2 aligned in the position directly over the opening 7A in the clip. The clip opening 7A as shown is capable of flexing to accept the entrance of rod into the interior opening of Clip 7 when a downward pressure is applied after rod 2 has been rotated into position to tighten the windlass mechanism. This embodiment would allow for the rod to be temporarily trapped on the interior of the opening and stay in position until an external force acted on it for the purpose of removing it.

Figure 17:
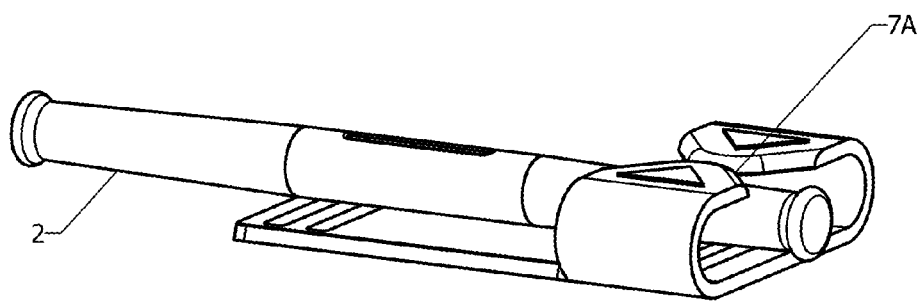
FIG. 17 is an isometric view of the clip and platform shown in FIG. 16 with the tensioning member secured in the clip.

FIG. 17 shows a situation in which rod 2 has been depressed downward, has flexed the edges of the clip opening 7A, bypassed those two edges, entered the interior, and is trapped in the cavity on the interior of the clip. For the purpose of removal, a similar force applied to the end of rod 2 would make it snap up and outward by overcoming the closing effect of the two sides of Clip 7 that form the opening. This is designed in such a way that by varying the opening the width of 7A different types of trapping features may be achieved. Moreover, embodiments may do away with a clipping action for holding it closed or a hook and loop type action for holding this opening closed by allowing that the sides of the clip that form the opening are made out of a material that is flexible but still resistant to an opening force that would allow them to act so as to trap the rod when inserted yet still be able to release the rod under a reasonable pressure to extract the rod from the internal opening of the Clip.

Figure 18:
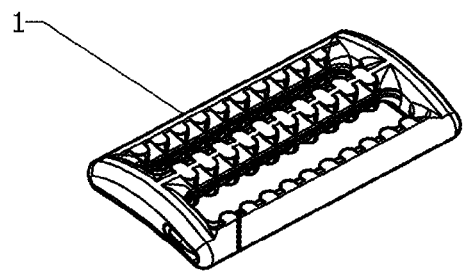
FIG. 18 is an isometric view of another exemplary buckle for use in a tourniquet assembly according to further aspects of the invention.

FIG. 18 shows an alternate embodiment of buckle 1. This embodiment shows that the buckle could have on its upper and lower surfaces a wide variety of different types of textured areas for the purpose of engaging lightly without damaging the webbing that is traced through it for the purpose of minimizing slippage. As can be seen in FIG. 18 there is also a slot, a pin, and a cavity located in the lower left side that will be discussed more in FIG. 19 but the orientation of this small slot and pin allow that buckle 1 could actually be designed so that a permanently sewn strap or folded over strap end could be attached or detached from this buckle with no additional modification of the strap or the buckle and for all intents and purposes this part could be considered interchangeable on any item that had a looped strapped end.

Figure 19:
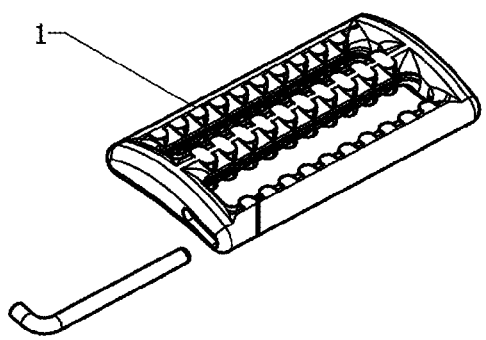
FIG. 19 depicts additional details of the exemplary buckle shown in FIG. 18 with a pin and associated webbing strip according to further aspects of the invention.
Figure 19:
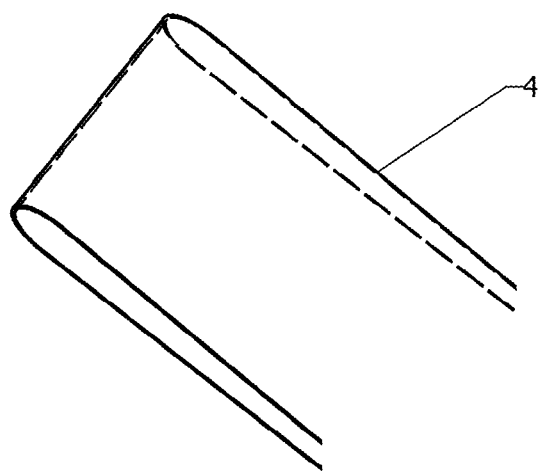

FIG. 19 shows additional details regarding this configuration. In FIG. 19, buckle 1 is shown with a slight open slit in the nearest buckle edge. This nearest buckle edge is understood to have a hole that runs through its length that is blind and does not exit the opposite end. On the end nearest the viewer you can see a cavity and located next to it is a pin. For exemplary purposes it will be considered that this pin could be made out of such a material as stainless or hardened steel. This pin could however be made out of a variety of materials that would suit the structural need.

Strap 4 is also shown in FIG. 19. The loop formed in strap 4 is configured such that, when the pin is removed, it can be entered through the slit shown in the center by lightly flexing out the edge of the buckle closest to the strap 4. The strap could then be placed in position so that it is trapped inside the buckle and the structural integrity of the unit returned by sliding the pin in through the cut area so that it completely crosses and enters into the edge of the buckle thereby eliminating the ability for the slanted cut edge to be opened and thereby forming a closed area for retention of the strap. The opening in the buckle that is shown on this edge corresponds to the curvature in the pin in such a way that when the pin is pressed into place a series of snap features in the plastic portion allow that the end of the pin can be depressed below the surface of the buckle and only removed by a small tool such as the tip of any standard pocket knife or any standard nail trimmer, etc. This would allow that the buckle 1 to become an interchangeable item, which will still act and function as a molded buckle, but also allow that different types of straps or features can be removed from it so that it is now considered interchangeable.

Figure 20:
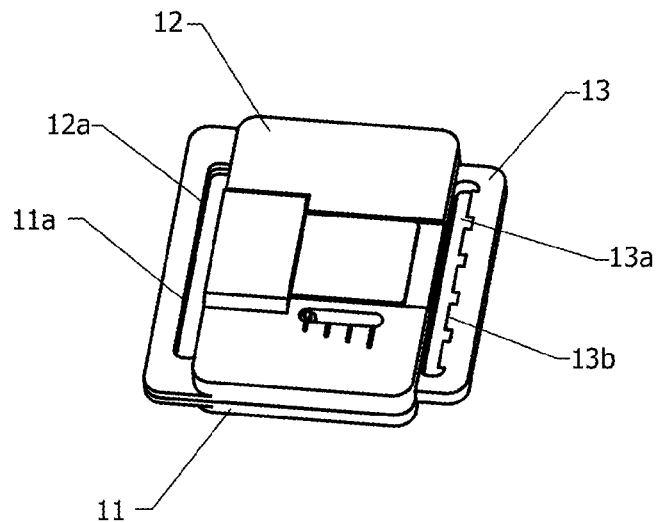
FIG. 20 is an isometric view of another exemplary tension indicator according to further aspects of the invention.

FIG. 20 shows a view of an exemplary tension indicator, specifically a PTID (Pressure & Time Indicator Device). The PTID is a device designed to allow tension applied to the openings in either side of it's body to initiate a timing mechanism as well as indicate that a force has been applied. FIG. 20 shows the bottom case half 11 in its assembled form.

Attachment Opening 12a, also shown in FIG. 1, for exemplary purposes only, is an area where a strap or other tension transfer device could be utilized to hold or apply pressure to the side of the mechanical assembly when bottom case half 11 and top case half 12 are assembled.

Also shown in FIG. 20 is the bottom case half attachment opening 11a, which when assembled will correspond with attachment opening 12a for the purpose of making an opening. Strapping, webbing, or another device could be installed through this opening to attach this device to a wide variety of different items that are designed to apply a linear pressure.

FIG. 20 also shows inner plate 13, which is shown to have on one of its edges inner plate attachment opening 13a, as well as the strap engagement feature—13b. Inner plate attachment opening 13a is designed so that a strap or other feature could be applied to this side of the device to apply tension.

Figure 21:
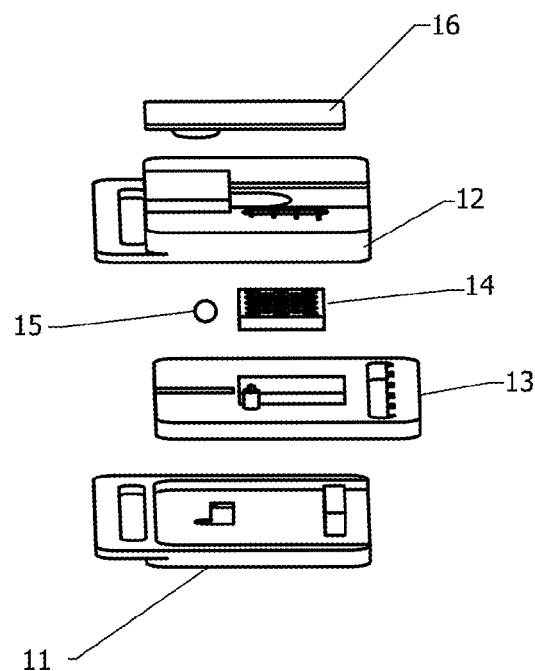
FIG. 21 depicts further details of component parts of the exemplary tension indicator shown in FIG. 20.

FIG. 21 shows an exploded view of the principal parts of the device. As shown in FIG. 21, bottom half case 11 is shown unassembled. The bottom half case 11 may be permanently connected to top case half 12. While these parts could be made from a wide variety of different materials necessary to suit their function, for this embodiment the device will be made of a non-metallic polymer that would allow permanent attachment of the bottom case half 11 and the top case half 12.

FIG. 21 also shows inner plate 13 shown in its oriented position. Shown slightly above inner plate 13 is compression block 14 and ball 15. These are shown in their correct orientation. Shown in the uppermost portion of FIG. 21 is time indicator 16.

Figure 22:
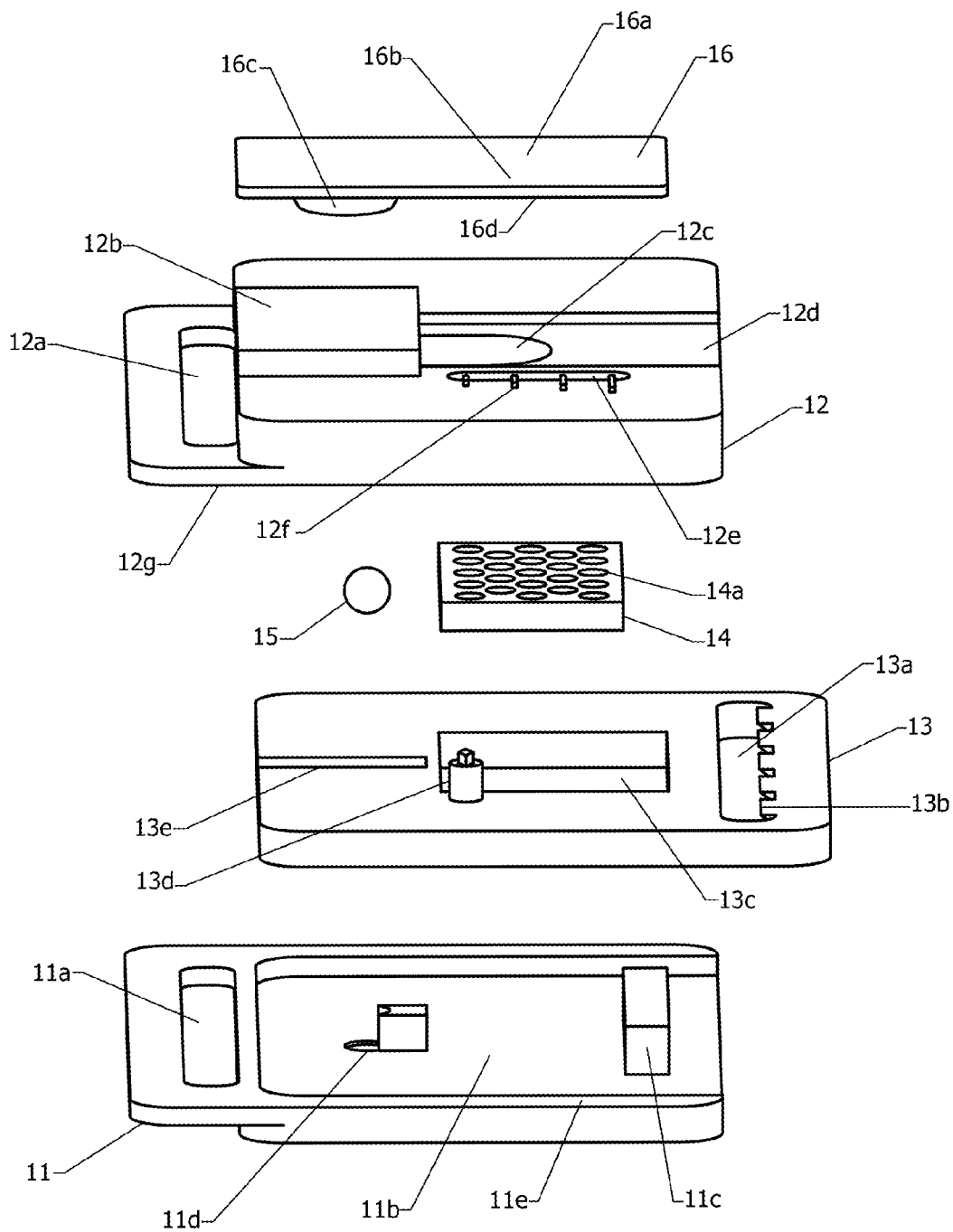
FIG. 22 is an enlarged view depicting further details of the exemplary tension indicator shown in FIG. 21 with additional subcomponents and features identified.

FIG. 22 shows an extensively labeled exploded view of the device for clarification of the diagrams that are to follow. Time indicator 16 can be any of a variety of different timing mechanisms whose purpose is to display visually or tactilely the elapsed time since the time of activation and/or reactivation. For the purpose of demonstration, we have illustrated a time indicator that utilizes a reservoir 16c that when depressed ruptures and allows the progression to be shown on timers area 16a. The visual scaling area 6b could be printed on the Time Indicator 16 in an area that will interact with the device.

The pressure sensitive adhesive area 16d, allows the time indicator 6 to be placed in position on the device maintaining a secure position while in use.

Top half case 12 includes attachment opening 12a, time indicator 12b, clearance area 12c, locator slot 12d, visual and tactile indicator slot 12e, visual and tactile indicators 12f, and the ultrasonic welding area 12g shown along the bottom portion of this entire part. Centered in FIG. 22 is compression block 14 and compression internal openings 14a, and Ball 15.

Inner plate 13, includes inner plate attachment opening 13a, strap engagement feature 13b, compression block opening 13c, visual and tactile indicator post 13d, and ball ramp area 13e. Bottom half case 11 includes bottom half case attachment 11a, recess 11b, stop bar 11c, ball locator 11d, and the ultrasonic welding area 11e which completes the upper surface.

It is assumed that if these parts were made of polymer or other material that could be ultrasonically welded, bottom half case 11, top half case 12, inner plate 13, compression block 14, and ball 15 could be placed into the relative position as shown in FIG. 13 and the exterior parts welded into an assembly that would allow movement of the internal mechanisms.

Figure 23:
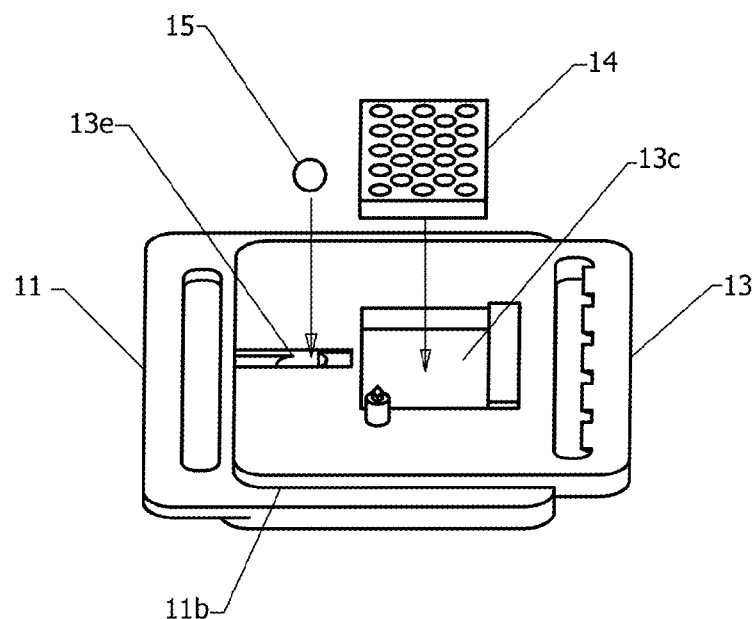
FIG. 23 is an isometric view of an exemplary base and moveable platform for use in the tension indicator shown in FIG. 20 with a moveable sphere and compression block.

FIG. 23 shows bottom half case 11 and inner plate 13 placed into the recess 11b. Compression block opening 13c is the area in which compression block 14 is placed. Also shown is ball 15 which will assume a position so that it is oriented in relationship to ball ramp area 13e.

Figure 24:
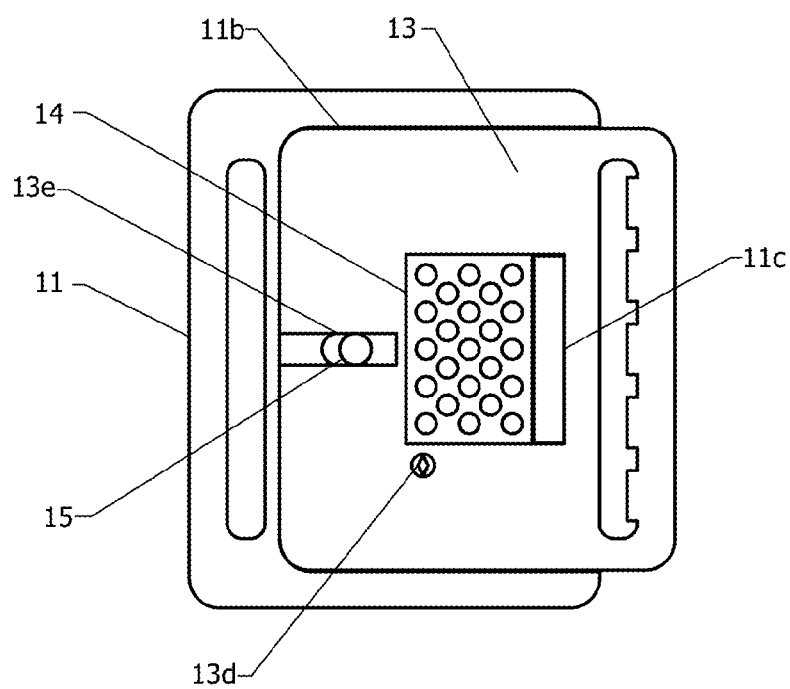
FIG. 24 is a top view of the base and moveable platform shown in FIG. 23 with the moveable sphere and compression block properly located.

FIG. 24 shows a top view of the components removed in FIG. 23 correctly positioned. Stop bar 11c rests against compression block 14 but applies no pressure until activated. Ball 15 is positioned in the ramp area but is not yet in contact with the ramp portion of ramp area 13e. When a strap or webbing mechanism applies force to the attachment points the following action will occur: First, there would be a compression of compress block 14 by stop bar 11c. The compression of compression block 14 allows lateral (i.e. horizontal in side view) travel of inner plate 13 along the recess in bottom half case 11 and recess 11b. Next, the ramp ball area 13e will come into contact with the ball thereby causing it to move upward (i.e. vertically in side view). This also causes lateral movement of the visual and tactile indicator post 13d in the same direction as the inner plate 13.

This compression of the compression block 14, movement of the visual and tactile indicator post 13d and the vertical displacement of ball 15 by a linear pressure applied to the slots on the side of this mechanism is a primary action of this device. This allows a controlled pressure to be continually applied once a tension has been exerted on the slots on each side of the device while movement of the ball 15 actuates a timer or other secondary device. The movement of visual and tactile indicator post 13d also reflects this action both tactilely and visually.

It should be noted that, although a spherical moveable member and ramp are described as a possible configuration for translating horizontal movement to vertical displacement, other configurations for accomplishing similar functions are contemplated within the scope of the invention including, for example, various rolling elements, asymmetrical moveable/rotatable members, stepped channels, etc.

Figure 25:
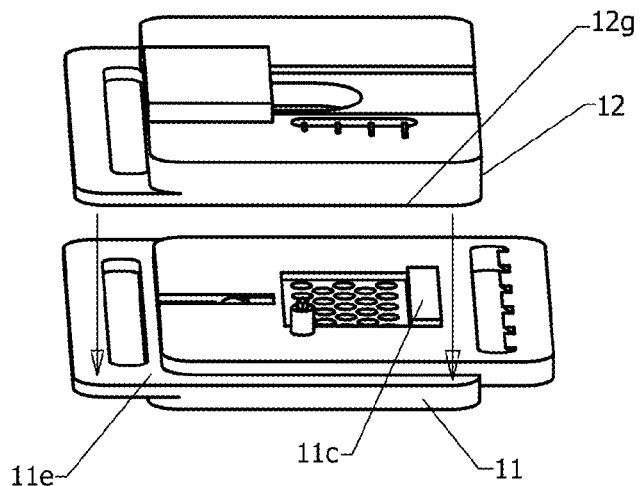
FIG. 25 is an isometric view including an exemplary top cover positioned over the base and moveable platform shown in FIG. 23.

In FIG. 25, ultrasonic welding area 11e shows the relationship to top half case 12 with its ultrasonic welding area 12g. Any alteration necessary for successful welding is embodied in this patent. Stop bar 11c is permanent position on top half case 12 during the assembly.

It is understood by having the bottom half case opening 11a and top half case attachment opening 12a together make up an opening. This is a security measure preventing failure by redundancy.

Figure 26:
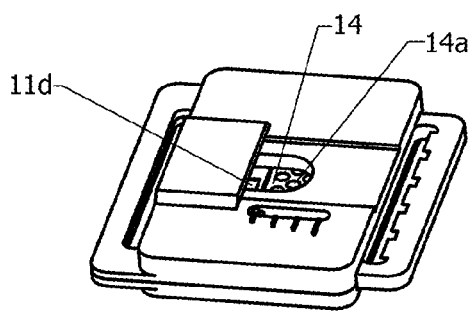
FIG. 26 is an isometric view of an assembled tension indicator including the top cover, base and moveable platform shown in FIG. 25 with the moveable sphere and compression block identified in the assembly.

FIG. 26 shows the unit assembled with time indicator 16 removed that allows one to see compression block 14 and the ball locator 11d through the center of this opening.

Figure 27:
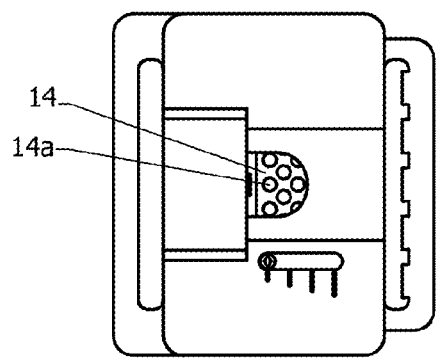
FIG. 27 is a top view of the assembled tension indicator including the top cover, base and moveable platform shown in FIG. 25.

FIG. 27 is a top view showing strap location, the compression block, and the mechanism ready to accept a time indicator 16 into position.

Figure 28:
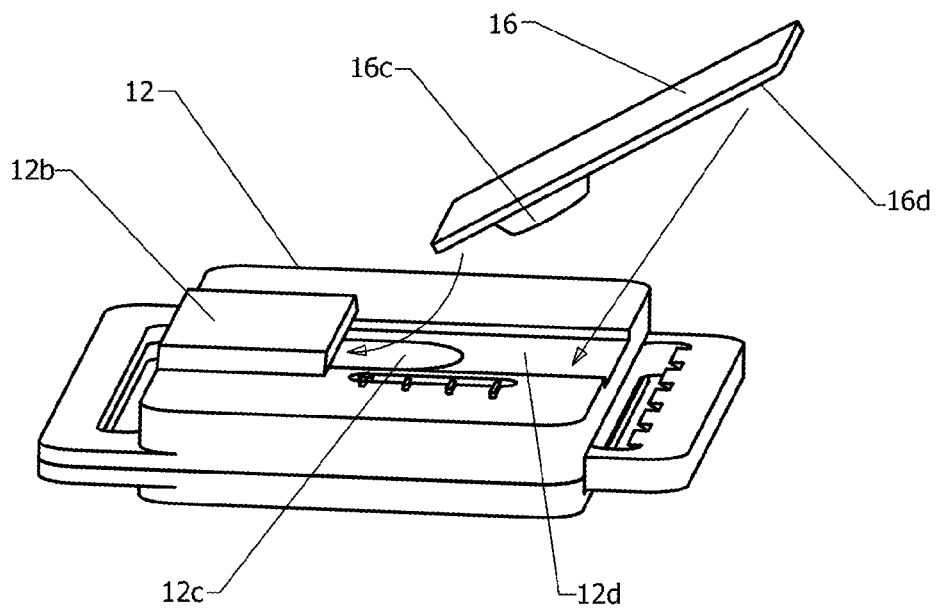
FIG. 28 is an isometric view showing the insertion of an exemplary visual indicator into the tension indicator shown in FIG. 25.

FIG. 28 shows the installation of this time indicator 16, which has on its lower surface, pressure sensitive adhesive 16d. The flexible time indicator can be loaded into the time indicator retainer 12b by moving through the clearance area 12c. This would then allow the intact reservoir 16c to be placed in the time indicator retainer 12b directly over ball 15 with no tension to inner plate 13. This can be done at various times after the initial assembly of the other components and may be done, for example, by a user of the tourniquet or a clinician.

The pressure sensitive adhesive 16d will adhere to the locator slot 12d. This completes the assembly with the time indicator 16 in position so that ball 15 applies pressure to reservoir 16c to actuate it. The upper surface of this area may be placed under a protective covering that may protect, shield, light, or magnify this area for the purpose of improved visibility of the indicators. Time indicator retainer 12b has enough room to accept, if needed, a wide variety of pressure sensitive devices, and can accept replaceable packages as may be desirable or necessary.

Figure 29:
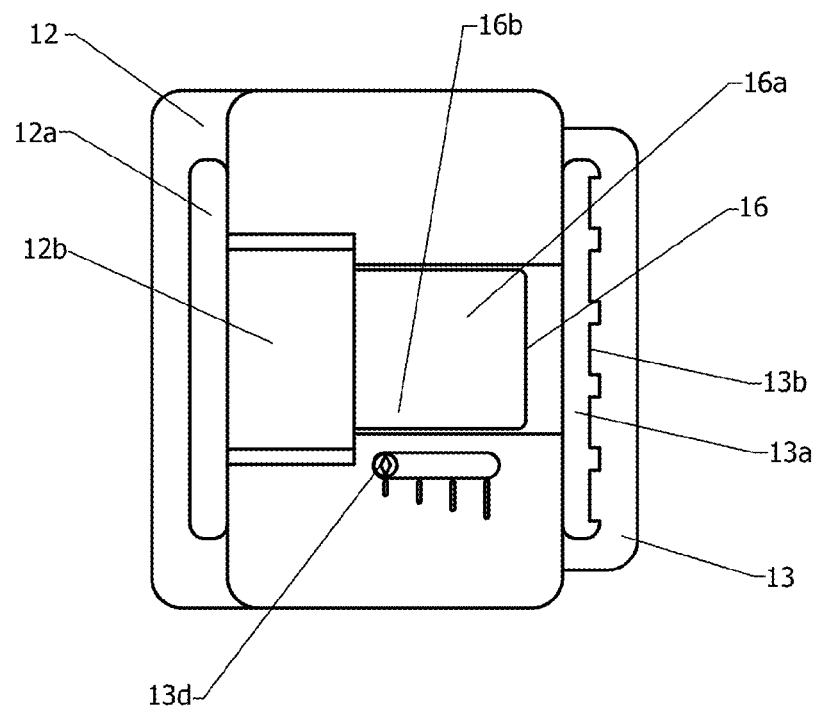
FIG. 29 is a top view of the tension indicator shown in FIG. 28 including the inserted visual indicator, and a tactile indicator which can be seen and felt through the top cover of the assembly shown in FIG. 25.

FIG. 29 shows the top view to illustrate the visual and tactile indicator post 13d. In FIG. 29, a printed visual used in the area of the visual graduated area 16b will correspond with the marker on top of the visual and tactile indicator post 13d. During the movement of the indicator post 13d both a tactile graduation can be felt through the top half case 12 as well as a series of printed information could also be placed in the visual graduation area 16b to help evaluate the degree of tension applied. It should be noted that a moveable tactile indicator can be disposed in various locations and orientations such as along the sides of the case components etc.

Figure 30:
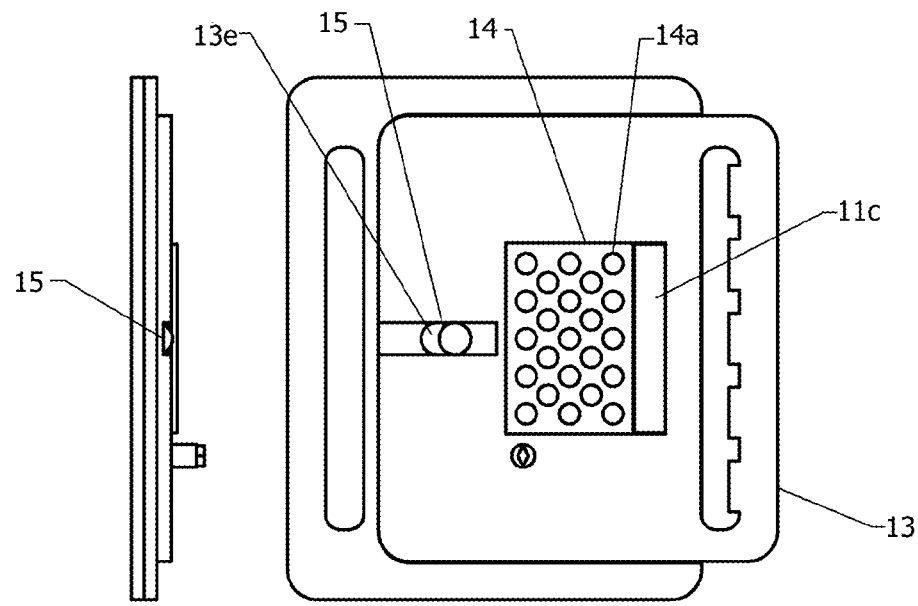
FIGS. 30 and 31 include a sequence of top views showing a relative motion between an exemplary base and moveable platform, along with an associated vertical displacement of the moveable sphere and compression of the compressible block.
Figure 31:
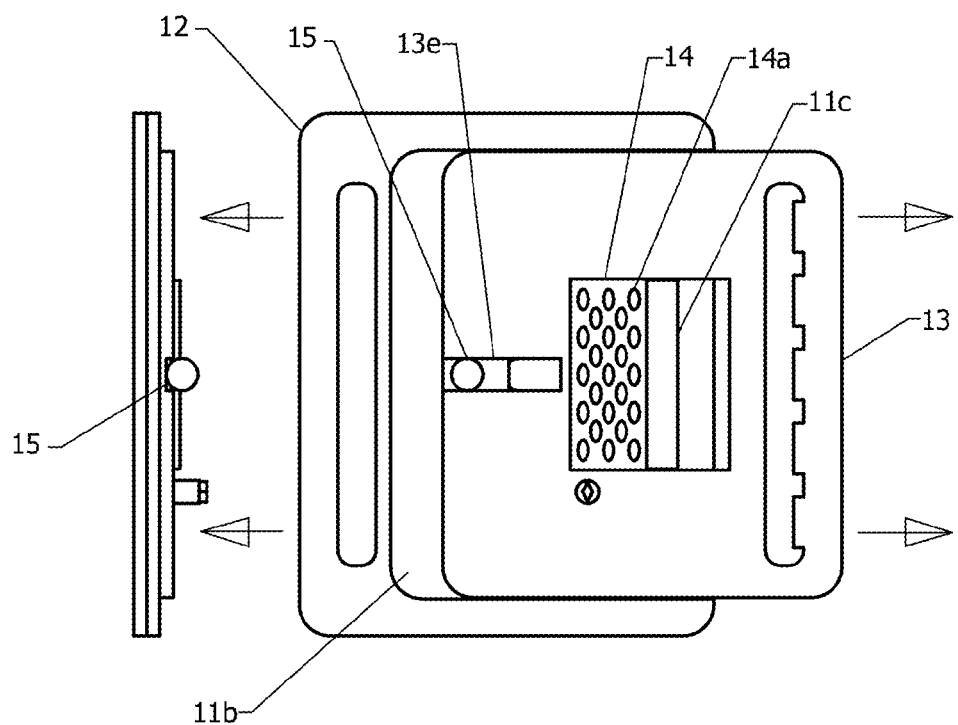

FIG. 30 and FIG. 31 are open top views accompanied by side views which demonstrate how the compression block 14 and movement of the elevation of ball 15 function. As seen in FIG. 30, the mechanism is not under tension initially. The compression block internal openings 14a are not deformed, the stop bar 11c is resting up against it and the ball 15 is shown not touching the ball ramp area 13e. FIG. 30 left-hand side view, shows ball 15 below the cutout surface. In FIG. 31, the arrows show that a tension is exerted in to separate the device. When a pressure is applied to these parts the force is inhibited by compression block 14, which is distorted. This movement forward of inner plate 13 in the recess 11b allows the ball 15, to be forced upward by the interaction of ramp 13e thereby pushing it upward while the inner plate 13 moves in a forward direction. The side view shows the current elevation in the position of ball 15. The elevation of ball 15 activates the time indicator 16 by crushing the reservoir by its elevation by ramp 13e.

Figure 32A:
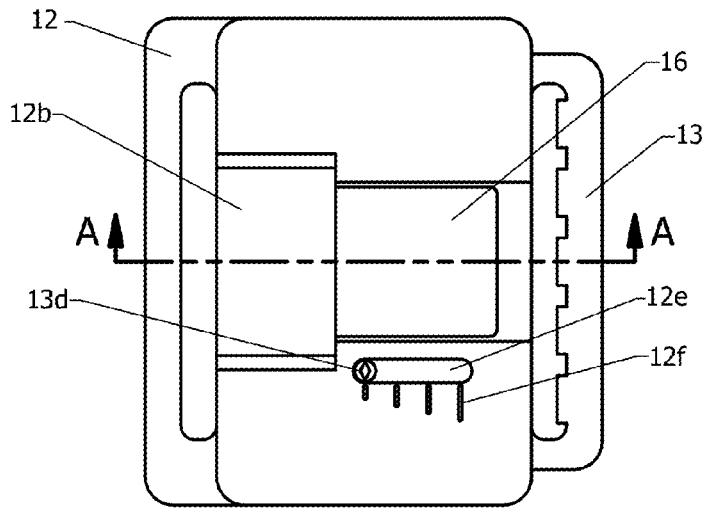
FIG. 32A is a top view of an exemplary tension indicator including a tactile indicator according to aspects of the invention.
Figure 32B:
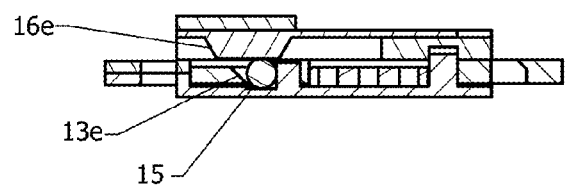
FIG. 32B is a cross sectional view of the tension indicator shown in FIG. 32A along line A showing the position of a moveable sphere.

FIG. 32 demonstrates an embodiment of this device by showing a top view of the relative components previously described and also a sectioned view. It is shown in this position without tension with ball 15 positioned directly below the undisturbed reservoir 16c.

Figure 33A:
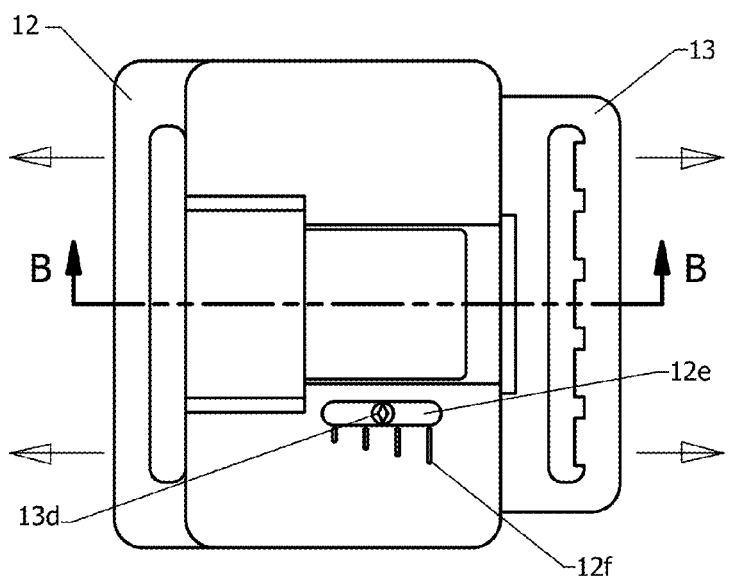
FIG. 33A is a top view of the tension indicator shown in FIG. 32A with the moveable platform pulled partly out of the assembly.
Figure 33B:
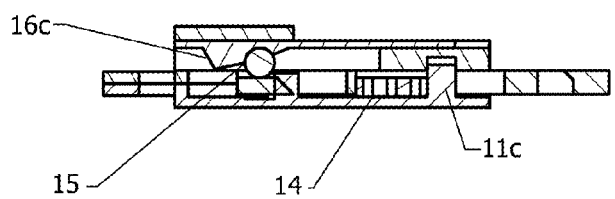
FIG. 33B is a cross sectional view of the tension indicator shown in FIG. 34A along line B showing an associated vertical displacement of the moveable sphere according to aspects of the invention.

In FIG. 33 the ball 15 has been forced upward by the movement of ball ramp area 13e thereby crushing the reservoir 16c. This will cause time indicator 16 to begin displaying a visual representation of the elapsed time. Also shown in FIG. 33 the indicator post 13d has moved from its position in FIG. 32 to its position in FIG. 33 that is showing a movement in relationship to the slot as well as now a visible indication of how far it has progressed according to visual and tactile indicator graduations 12f.

It is also seen that all of this is held in a state of restraint by the action of stop bar 11c restraining the movement of compression block 14 when a tensile pressure is applied to the openings on each side of the mechanism. The relationship to this particular mechanism when a strap is applied to each side of it, a pressure is applied to each of those straps, a small polymer block filled with openings acts as a compression device for the purpose of allowing a tensile pressure to be applied in a consistent graduated manner that can be maintained due to the compression of the block. The actuation of this unit also allows a physical movement to operate a wide variety of different types of visual timing features as well as any other type of physical pressure sensor that could be actuated by the vertical movement of a ball in a crushing feature against a solid restraint. The item also has a visual and tactile indicator post that is set up for the purpose of allowing the user to feel the amount of movement and thereby be able to approximate the amount of tension that has been placed on the device. It is understood that when a tension is applied to these two items that it will begin with an ever increasing amount of pressure that can continually be maintained to the item for a wide variety of different purposes.

Figure 34:
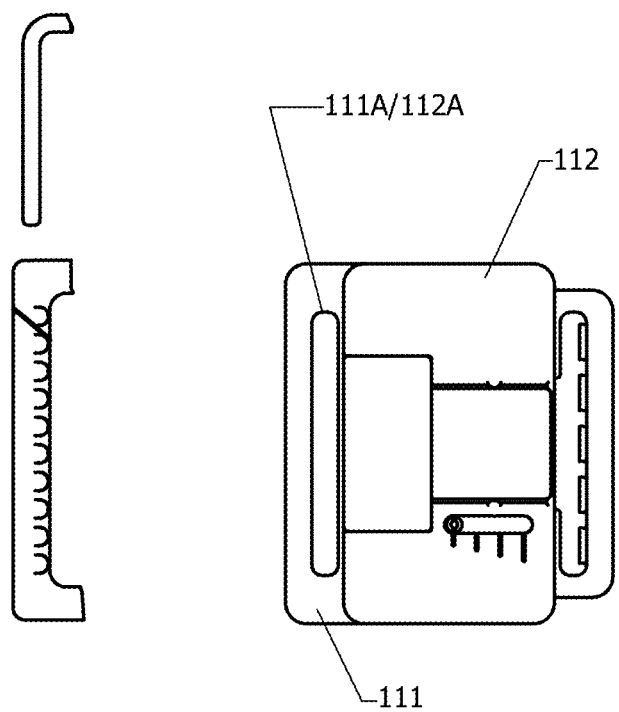
FIG. 34 is a top view of another exemplary tension indicator according to further aspects of the invention.

FIG. 34 shows the possible embodiment of an attachment opening that could be added to devices described herein. FIG. 34 shows that if bottom half case 111 and top half case 112 are assembled they generate the opening shown by the leader that calls out bottom half case opening 111A and top half case opening 112A shown in the right hand view of the device to be a closed area. On the left of FIG. 34 is shown an embodiment that the opening 111A, 112A could be manufactured in such a way that a series of protruding ridges assisted in the capture of the strapping material for the purpose of minimizing its movement past this point as well as that a slot with an accompanying pin could be added to the manufacture of the device so that a strap could be slid through the slot shown in the left hand portion of FIG. 34 and then a steel or other type of pin slid through the a hole in that existing part for the purpose of closing it temporarily yet securely. This would allow the device to then have a pin removed, a piece of permanently looped strapping slid through an opening, and the pin replaced for the purpose of allowing the unit to be considered to be interchangeable at that point.

Figure 35:
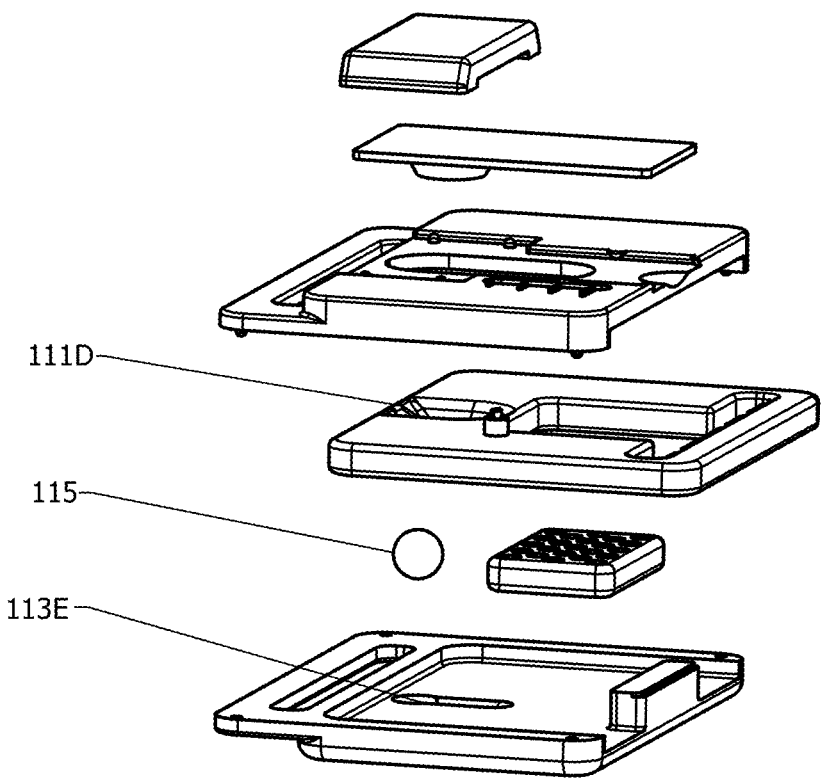
FIG. 35 is an isometric view of another exemplary tension indicator showing component parts according to further aspects of the invention.

FIG. 35 shows a possible embodiment in which the way the ball 115 is elevated to perform the functions necessary in relationship to the operation of the device as previously described. A ball ramp area 113E could be designed in such a way that it includes a semi-spherical depression attached to a trough so that the ball resides in the ball ramp area semi-spherical depression. When ball locator 111D is placed in the correct position, movement in a linear direction of ball locator 111D would raise the ball from its given position in the semi-spherical depression and allow it to roll forward along the trough at an elevated height from where it is normally at rest. This will be explained in further detail in following features.

Figure 36:
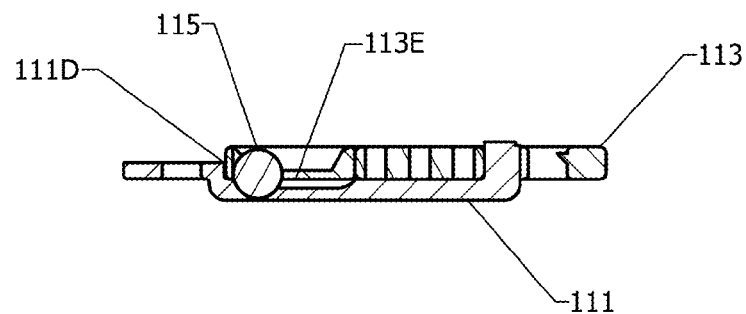
FIG. 36 is a cross sectional view of base and moveable platform as used in the tension indicator shown in FIG. 35 including the position of a moveable sphere.

FIG. 36 shows the cutaway views of possible embodiment of the device shown in FIG. 35 showing very clearly that ball 115 is at rest in a depression in the ball ramp area 113E. It is shown that when pressure is applied in a linear fashion to inner plate 113, a linear pull on inner plate 113 would cause the ball ramp area 113E by movement of inner plate 113 to have ball locator 111D apply pressure on the back side of the ball thereby forcing the ball to move vertically as inner plate 113 moves in a linear fashion.

Figure 37:
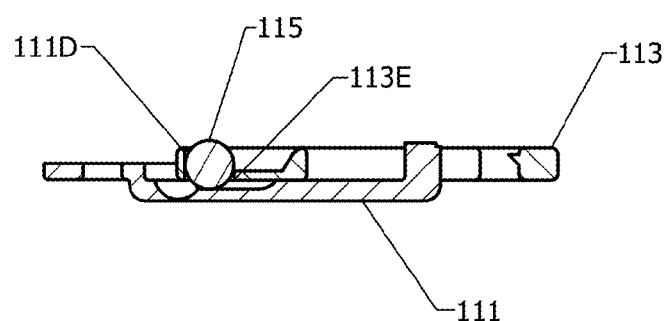
FIG. 37 is a cross sectional view of the base and moveable platform shown in FIG. 36 showing the moveable platform pulled partly away from the base and an associated horizontal and vertical displacement of the moveable sphere according to aspects of the invention.

FIG. 37 shows that a linear pull has been applied to inner plate 113, has moved in a linear fashion so that ball 115 no longer rests in its normal position in ball ramp area 113E but has been elevated by the pressure acting on it from ball locator 111D. This embodiment shows another way in which the ball could be elevated for the purpose of activating parts of the device as previously described.

Figure 38:
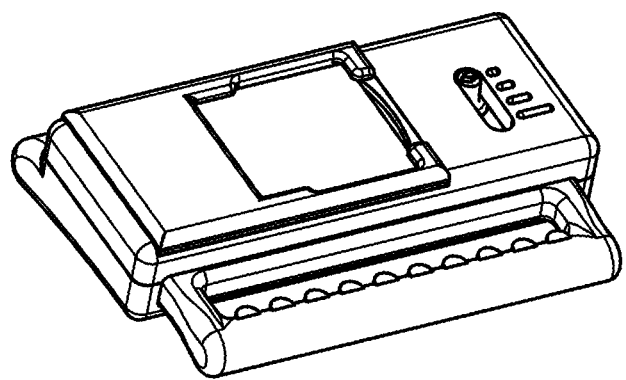
FIGS. 38 and 39 are isometric views of another exemplary tension indicator according to further aspects of the invention.

FIG. 38 shows an embodiment of the device in which the time indicator has been turned 90-degrees from the previously described art. This embodiment would allow the PTID could be much more narrowly made by increasing its height while still fitting all the vital functions into it. This embodiment would allow the maximization of the previously described function of the device in a much smaller area. Also shown in FIG. 38 is the series of protruding ridges on the strap-locating feature that show an alternate embodiment compared to the earlier description.

Figure 39:
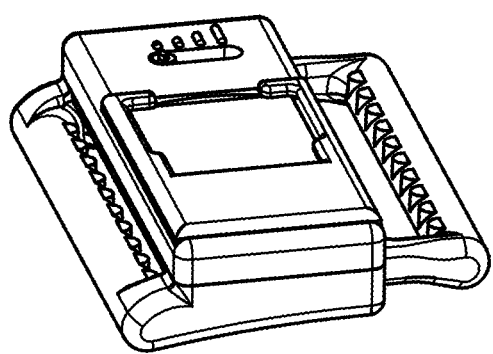

FIG. 39 shows another view of the device which shows that it functions in the same fashion basically an inner plate trapped on the interior acts against a compression block allowing strapping attached either permanently or by virtue of a system described in FIG. 34 would allow a strap placed on either side when tension is applied to it would not only provide a compressive force due to the interior workings of the device but a visual indicator as well as actuate a mechanical movement that activates a timed device.

Figure 40:
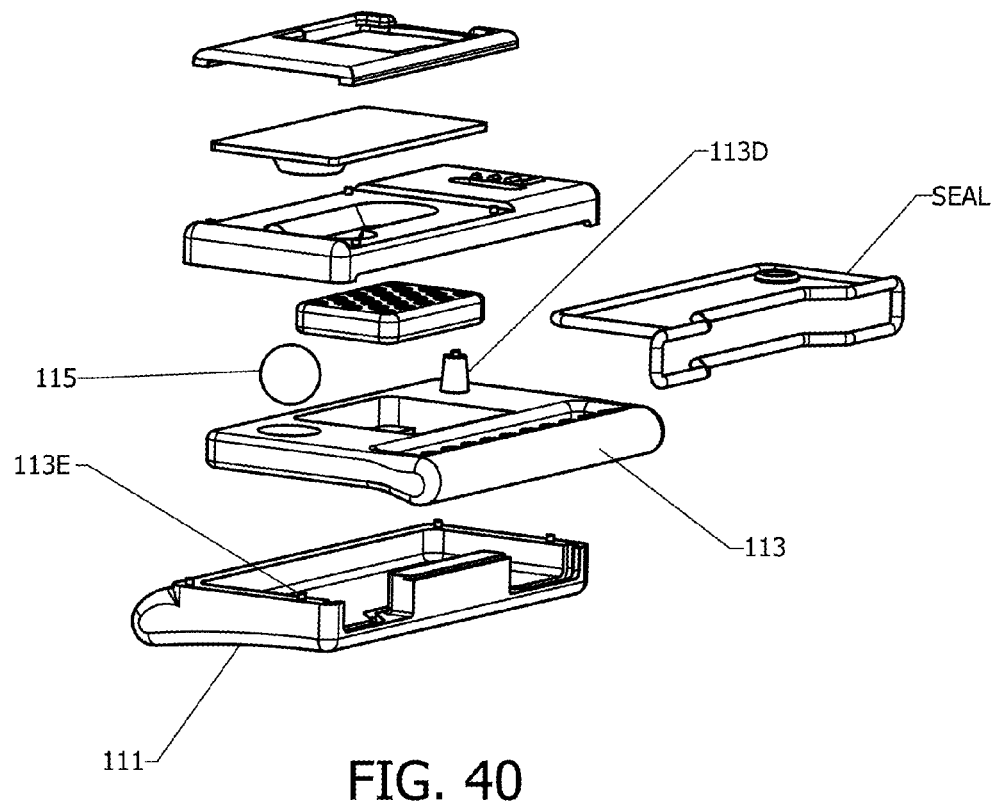
FIG. 40 depicts further details of component parts of the exemplary tension indicator shown in FIGS. 38 and 39.

FIG. 40 shows an exploded view of the embodiment shown in FIGS. 38 & 39 that shows an additional possible embodiment in which case there has been a seal feature added. The seal feature is designed for applications when the device would need to be dust resistant, water resistant and still have the capability to be stored for extended periods of time in harsh conditions and still activate without foreign material to penetrate the case and thereby possibly prevent it from carrying out its mechanical function. Ball 115 is shown resting above its semi-spherical depression.

FIG. 40 also shows ball ramp area 113E shown in the bottom portion of bottom half case 111, inner plate 113E is in its correct position and indicator post 113D. The seal shown is designed to be inserted between the upper & lower portions of the device during assembly. The seal is made of a flexible material, which would have the capacity to act as a seal or gasketing material when compressed. The seal shown has at its center a thin membrane capable of sealing but also capable of having things actuated through this thin membrane while maintaining a seal from the exterior environment. The seal has a raised rounded rib around its outside edge similar to an 0-ring that performs the same function in a gasketing capacity. The seal has a raised ridged perforation in its center similar to a grommet. This grommet fits over a tapered round post.

The tapered round post is shown as indicator post 113D which allows this hard physical feature could penetrate the membrane while still allowing the membrane to seal around it and the interior of the device. The front portion of the seal as shown in FIG. 40 has a shaped opening through it, that is bound on its circumference by a rounded portion similar to a shaped 0-ring. This shaped 0-ring is designed so that when inner plate 113 passes through this area and the upper and lower portions of the device are permanently assembled, the 0-ring shown in the front portion of the seal will fit snuggly around the inner plate, fit into a series of grooves in the upper and lower portions of the device, and upon permanently assembly this opening in the front portion of the seal will act as a gasket or seal the moving inner plate during its movement cycle in and out.

Figure 41:
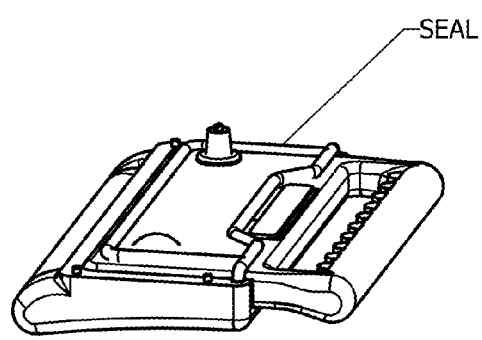
FIG. 41 depicts further details the exemplary tension indicator shown in FIGS. 38 and 39 including an internal seal.

FIG. 41 shows the applications of the seal. The seal shown in this view has the grommet portion placed over part 113D and is sealing it accordingly. The exterior portion of the seal is in position in this bottom portion where the top portion needs to be installed. The raised outer ridge is placed in the correct grooves or touching the correct gasketing surfaces. Ball 115 is also shown, during its assembly, while resting in its semi-spherical position is protruding up slightly through the gasketing thin membrane, which covers the center of the seal. This allows that once assembled, the ball will remain on one side of the membrane by virtue of the membrane's qualities, but will be able to have the ball protrude up, push on the membrane, and ultimately activate the time indicator device through the membrane while still maintaining a seal from the exterior that will prevent the possibility of foreign matter entering the interior of the device and prevent interference with its mechanical function. The seal is designed so that it has good storage life, flexibility, and elasticity necessary to perform its functions. It not only acts as a seal around the various moving portions of this but is also designed as described earlier to allow the ball to activate a physical feature through it and return to an at rest position as well as allowing the indicator post 113D to move in a linear fashion forward and backward while still maintaining a seal due to the grommet feature enclosing the post and flexibility and elasticity of the material sealed material around it. This gasket may be installed permanently during the final assembly and act in accordance with its needs as a gasketing and sealing device.

The description and examples given above are merely illustrative and are not meant to be an exhaustive list of all possible embodiments, applications or modifications of the invention.

Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the medical sciences, orthopedic surgery, or related fields are intended to be within the scope of the appended claims.

The disclosures of all references and publications cited above are expressly incorporated by reference in their entireties to the same extent as if each were incorporated by reference individually.

What is claimed is:

1. A tourniquet assembly comprising:
   a pressure applicator adapted to be secured around a limb;
   a tensioning mechanism for applying a working tension to the pressure applicator, the tensioning mechanism including a platform, a clip and a tensioning member; wherein, the tensioning mechanism is configured to apply the working tension via rotation of the tensioning member, and the clip is configured to receive, and at least temporarily inhibit rotation of, the tensioning member; and
   a tension indicator, wherein said tension indicator comprises:
      a base configured to attach to the pressure applicator;
      a tension indicator platform configured to move relative to the base when subjected to the working tension;
      a tactile indicator configured to provide a variable tactile indicator based on relative lateral motion of the platform to the base;
      a visual indicator configured to provide a variable visible indicator based on the working tension, wherein:
         said visual indicator comprises a reservoir, a timing strip, and a seal between the reservoir and the timing strip; and
      an initiator configured to apply a variable pressure to the visual indicator based on relative lateral motion of the tension indicator platform to the base, wherein:
         said initiator includes a moveable member that is configured to apply the variable pressure to the reservoir via vertical displacement of the moveable member in response to the relative lateral motion of the tension indicator platform to the base.

2. The tourniquet assembly of claim 1, wherein said pressure applicator includes a plurality of strips including a tensioning strip that is received through the tensioning member.

3. The tourniquet assembly of claim 1, wherein said platform includes at least one first slot sized to receive at least part of the pressure applicator therethrough.

4. The tourniquet assembly of claim 3, wherein:
   said first slot is disposed toward one end of the platform and said clip is disposed toward the other end of the platform; and said tensioning member is disposed between the first slot and the clip.

5. The tourniquet assembly of claim 1, wherein said clip is configured to transition from an open configuration that allows the tensioning member to be received in the clip, to a closed configuration that holds the tensioning member from being released from the clip.

6. The tourniquet assembly of claim 5, wherein said clip includes opposing flexible walls and a pair of opposing flanges disposed on free ends of respective opposing walls, each of said flanges being configured to selectively engage with the other opposing flange to at least temporarily secure the clip in the closed configuration.

7. The tourniquet assembly of claim 5, wherein said clip includes a slot for receiving the tensioning member and a flap that is configured to close the slot in the closed configuration.

8. The tourniquet assembly of claim 1, wherein the pressure applied to the reservoir via the moveable member is operable to force a fluid contained in the reservoir through the seal and into communication with the strip.

* * * * *